(12) United States Patent
McTavish

(10) Patent No.: US 6,673,582 B2
(45) Date of Patent: Jan. 6, 2004

(54) MICROBES AND METHODS FOR REMEDIATION

(75) Inventor: Hugh McTavish, Birchwood, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 0 days.

(21) Appl. No.: 09/769,719

(22) Filed: Jan. 25, 2001

(65) Prior Publication Data

US 2002/0098574 A1 Jul. 25, 2002

Related U.S. Application Data

(60) Provisional application No. 60/178,345, filed on Jan. 25, 2000.

(51) Int. Cl.$^7$ .......................... C12P 17/12; C12N 11/16
(52) U.S. Cl. .................. 435/122; 435/252.33; 435/195; 435/252.1; 435/177
(58) Field of Search ........................... 435/122, 252.33, 435/195, 252.1, 177

(56) References Cited

U.S. PATENT DOCUMENTS

| | | | |
|---|---|---|---|
| 3,779,869 A | 12/1973 | Zienty | 195/65 |
| 3,957,580 A * | 5/1976 | Nelson | 195/31 R |
| 4,075,321 A | 2/1978 | Relyveld | 424/92 |
| 4,138,290 A | 2/1979 | McMullen et al. | 195/317 |
| 4,695,455 A * | 9/1987 | Barnes et al. | 424/93 |
| 4,745,064 A | 5/1988 | Cook et al. | 435/252 |
| 4,757,008 A | 7/1988 | Reverman | 435/94 |
| 4,798,786 A | 1/1989 | Tice et al. | 435/177 |
| 4,849,217 A | 7/1989 | Soares et al. | 424/93 |
| 4,918,016 A | 4/1990 | Leuba et al. | 435/176 |
| 5,073,677 A | 12/1991 | Helmer et al. | 800/205 |
| 5,143,847 A | 9/1992 | Kawase et al. | 435/288 |
| 5,318,913 A | 6/1994 | Relyveld | 436/520 |
| 5,429,949 A | 7/1995 | Radosevich et al. | 435/252.1 |
| 5,437,993 A | 8/1995 | Visuri | 435/234 |
| 5,474,925 A | 12/1995 | Maliyakal et al. | 435/172.3 |
| 5,489,401 A | 2/1996 | Freeman | 264/4.3 |
| 5,508,193 A | 4/1996 | Mandelbaum et al. | 435/253.3 |
| 5,824,512 A | 10/1998 | Pazirandeh et al. | 435/64.7 |
| 5,849,296 A | 12/1998 | Navia et al. | 424/178.1 |
| 6,265,201 B1 | 7/2001 | Wackett et al. | 435/252.7 |
| 6,284,522 B1 | 9/2001 | Wackett et al. | 435/262.5 |
| 6,369,299 B1 | 4/2002 | Sadowsky et al. | 800/298 |
| 2002/0039778 A1 | 4/2002 | Wackett et al. | 435/196 |
| 2002/0045236 A1 | 4/2002 | Wackett et al. | 435/195 |
| 2002/0098574 A1 | 7/2002 | McTavish | 435/262.5 |

FOREIGN PATENT DOCUMENTS

| | | |
|---|---|---|
| DE | 35 08 906 A1 | 9/1986 |
| EP | 141 784 A1 | 10/1984 |
| EP | 218 571 A2 | 4/1987 |
| EP | 234 415 A2 | 9/1987 |
| EP | 302 284 B1 | 2/1989 |
| EP | 0 340 378 A1 | 11/1989 |
| EP | 340 378 B1 | 11/1989 |
| EP | 859 051 A1 | 8/1998 |
| EP | 0 859 051 B1 | 1/2002 |
| GB | 2 244 711 A | 12/1991 |
| JP | 616 9772 | 6/1994 |
| RU | 20 90 246 C1 | 9/1997 |
| WO | 97/15675 | 5/1997 |
| WO | WO 98 18941 | 5/1998 |
| WO | 98/31816 | 7/1998 |

OTHER PUBLICATIONS

DeSouza, M.L., et al. (1996) J. Bacteriol. 178(16), 4894–4900.*

Nagy et al., "A Single Cytochrome P–450 System is Involved in Degradation of the Herbicides EPTC (S–Ethyl Dipropylthiocarbamate) and Atrazine by Rhodococcus sp. Strain NI86/21," Applied and Environmental Microbiology, 61(5), 2056–2060 (1995).

Armstrong et al., "Adsorption catalyzed chemical Hydrolysis of Atrazine," *Environ Sci Technol.* 1968;2:683–689.

Ausubel, et al., eds., *Current Protocols in Molecular Biology*, John Wiley & Sons, Inc., United States; title page, publication page, and table of contents only: 12 pages (1994).

Behki et al., "Degradation of atrazine by Pseudomonas: N–Dealkylation and dehalogenation of atrazine and its metabolites," *J Agric Food Chem.* 1986;34: 746–749.

Behki et al., "Metabolism of the herbicide atrazine by rhodococcus strains," *Appl Environ Microbiol.* 1993;59:1955–1959.

Box, et al., *Statistics for experimenters: an introduction to design, data analysis, and model building*, John Wiley & Sons, Inc., New York, NY; title page, publisher's page and table of contents only: 10 pages (1978).

Brosius, et al., "Gene organization and primary structure of a ribosomal RNA operon from *Escherichia coli*," *J Mol Biol.* May 15, 1981;148(2):107–27.

Burchfield et al., "Pyridine–alkali reactions in the analysis of pesticides containing active halogen atoms," *Agricultural and Food Chemistry*. 1958;6:106–110.

Caldwell et al., "Limits of Diffusion in the Hydrolysis of Substrates by the Phosphotriesterase from *Pseudomonas diminuta*," *Biochem.* 1991;30(30):7438–7444.

Cook "Biodegradation of s–triazine xenobiotics," *FEMS Microbiol Rev.* 1987;46:93–116.

Cook et al., "s–Triazines as Nitrogen Sources for Bacteria," *J Agric Food Chem.* 1981;29:1135–1143.

(List continued on next page.)

Primary Examiner—Charles L. Patterson, Jr.
(74) *Attorney, Agent, or Firm*—Mueting, Raasch & Gebhardt, P.A.

(57) ABSTRACT

The present invention provides methods of using a microbe containing a polypeptide that degrades, preferably detoxifies, a compound that is present in the environment. Preferably, the polypeptide is a hydrolase and the compound is at least one s-triazine. The present invention also provides a microbe containing a polypeptide that degrades, preferably detoxifies, a compound that is present in the environment.

14 Claims, 7 Drawing Sheets

OTHER PUBLICATIONS de Souza et al., "Identification of a Gene Cluster from *Pseudomonas* sp. ADP, Involved in Atrazine Biodegradation," Abstracts of the 95$^{th}$ General Meeting of American Society for Microbiology 1995, abstract Q–89, 415 (May 21–25, 1995).

de Souza et al., "Cloning, characterization, and expression of a gene region from Pseudomonas sp. strain ADP involved in the dechlorination of atrazine," *Appl Environ Microbiol.* Sep. 1995; 61(9):3373–8.

Eaton et al., "Metabolism of dibutylphthalate and phthalate by Micrococcus sp. strain 12B," *J Bacteriol.* Jul. 1982; 151(1):48–57.

Eaton et al., "Cloning and comparison of the DNA encoding ammelide aminohydrolase and cyanuric acid amidohydrolase from three s–triazine–degrading bacterial strains," *J Bacteriol.* Feb. 1991; 173(3):1363–6.

Eaton et al., "Cloning and analysis of s–triazine catabolic genes from Pseudomonas sp. strain NRRLB–12227," *J Bacteriol.* Feb. 1991;173(3):1215–22.

Erickson et al., "Degradation of atrazine and related s–triazines," *Critical Rev Environ Cont.* 1989; 19(1):1–13.

Fadullon et al., "Degradation of atrazine in soil by Streptomyces," *J Environ Sci Health B.* Jan. 1998;33(1):37–49.

Flores et al., "Characterization of a glutaraldehyde stabilized yeast cell biocatalyst with β–galactosidase activity," *J Ferment Bioeng.* 1996;81(6):524–29.

Freeman et al., "Fixation and stabilization of *Escherichia coli* cells displaying genetically engineered cell surface proteins," *Biotechnol Bioeng.* 1996;52(5):625–30.

Giardina et al., "4–Amino–2–chloro–1,3,5–triazine: A new metabolite of atrazine by a soil bacterium," *Agric Biol Chem.* 1980;44:2067–2072.

Jessee et al., "Anaerobic degradation of cyanuric acid, cysteine, and atrazine by a facultative anaerobic bacterium," *Appl Environ Microbiol.* 1983;45(1):97–102.

Jones et al., "Degradation of atrazine in estuarine water/sediment systems and soils," *J Environ Qual.* 1982;11(4):632–638.

Kauffmann et al., "Entrapment of atrazine chlorohydrolase in sol–gel glass matrix," *J Biotech.* Jul. 16, 1998;62(3):169–176.

Kennedy et al., "Principles of immobilization of enzymes," *Handbook of Enzyme Biotechnology, 3$^{rd}$ Edition*, Wiseman, ed., Ellis Horwood Limited, Hertfordshire, Great Britain (1995) pp. 235–310.

Kontchou et al., "Rapid biodegradation of the herbicide atrazine in soil inoculated with a pure bacterial culture," Proceedings of the IX Simposium of Pesticide Chemistry: Mobility and Degradation of Xenobiotics, (A.A.M. Del Re et al., eds.), Piacenza, Italy, Oct. 11–13, 1993, pp. 533–536 (Instituto di Chimica Agraria ed Ambientale, Universit`` Cattolica del Sacro Cuore).

Koskinen et al., "Automation of atrazine and alachlor extraction from soil using a laboratory robotic system," *Soil Sci Soc Am J.* 1991;55:561–562.

LeBaron, "Ways and means to influence the activity and the persistence of triazine herbices in soils," *Residue Rev.* 1970;32:311–353.

Liu et al., "Ecology and evolution of microbial populations for bioremediation," *Trends Biotechnol.* Aug. 1993;11(8):344–52.

Maleki et al., "Degradation of atrazine by soil consortia: characterization of enzymatically active fractions from cell-bound and cell–free enrichment cultures," *Abstracts of the 95$^{th}$ General Meeting of the American Society for Microbiology*, Abstract No. Q–88, 415 (1995).

Mandelbaum et al., "Isolation and Characterization of Pseudomonas sp. That Mineralizes the s–Triazine Herbicide Atrazine," *Appl Environ. Microbiol.*, 1995;61:1451–1457.

Mandelbaum et al., "Rapid Hydrolysis of Atrazine to Hydroxyatrazine by Soil Bacteria," *Environ Sci Technol.* 1993;27:1943–1946.

Mandlebaum et al., "Mineralization of the s–triazine ring of atrazine by stable bacterial mixed cultures," *Appl Environ Microbiol.* Jun. 1993;59(6):1695–701.

Mattan, Cynthia "Dechlorination of Atrazine by the Enzyme atrazine Chlorohydrolase During Simulated Water Treatment Processes," Master of Sciences Thesis, University of Minnesota, 48 pages (1998).

Mosbach et al., eds., *Methods in Enzymology vol. 135. Part B. Immobilized Enzymes and Cells*, Academic Press, Orlando, FL; title page, publication page, and table of contents only: 5 pages (1985).

Mulchandani et al., "Detoxification of organophosphate nerve agents by immobilized *Escherichia coli* with surface-expressed organophosphorous hydrolase," *Biotechnol Bioeng.* Apr. 20, 1999;63(2):216–23.

Mulbry, "Purification and characterization of an inducible s–triazine hydrolase from *rhodococcus corallinus* NRRL B–15444R," *Appl Environ. Microbiol.* 1994;60(2):613–618.

Nair et al., "Effect of two electron acceptors on atrazine mineralization rates in soil," *Environ Sci Technol.* 1992;26(11):2298–2300.

National Institutes of Health, "BLAST 2 Sequences," [online] United States; retrieved Nov. 26, 2001, from the Internet: <URL:http://www.ncbi.nlm.nih.gov/gorf/bl2.html>, 1 page.

National Center for Biotechnology Information, National Library of Medicine, National Institutes of Health, GenBank Locus No. PAU55933, Accession No. U55933, "Pseudomonas ADP atrazine chlorohydrolase (atzA) gene, complete cds," [online]. Bethesda, MD [retrieved on Jan. 2, 2001]. Retrieved from Internet URL:<www.ncbi.nlm.nih.gov/entrez/query.fcgi?cmd=Retrieve&db=Nucleotide&list_uids=3766245&dopt=GenBank>, 2 pages.

National Center for Biotechnology Information, National Library of Medicine, National Institutes of Health, GenBank Locus No. AAC64663, Accession No. AAC64663, "atrazine chlorohydrolase [Pseudomonas sp. ADP],"[online]. Bethesda, MD [retrieved on Jan. 2, 2001]. Retrieved from Internet URL:<http://www.ncbi.nlm.nih.gov/entrez/query.fcgi?cmd=Retrieve&db=Protein&list _uids=3766246&dopt=GenPept>, 2 pages.

Olsen "Removal of Atrazine from Drinking Water Using Cross–linked Cells in Alginate Beads," *Fall 2000 Newsletter*, [online] Hamline University Biology Department, Saint Paul, MN [retrieved on Dec. 4, 2001]. Retrieved from Internet URL<http://138.192.68.68/bio/faculty/malody/bioalumpage/ bioalumpage/newsletters/newsletterF00.htm#Biology>, 5 pages.

Radosevich et al., "Degradation and mineralization of atrazine by a soil bacterial isolate," *Appl Environ Microbiol.* Jan. 1995;61(1):297–302.

Radosevich et al., "Biodegradation of atrazine in surface soils and subsurface sediments collected from an agricultural research farm," *Biodegradation.* Apr. 1996;7(2):137–49.

Sambrook et al., *Molecular Cloning, a Laboratory Manual, 2nd Edition*, Cold Spring Harbor Laboratory Press, Cold Spring Harbor, New York; title page, publication page and table of contents only: 30 pages (1989).

Sadowsky et al., "Use of Phytoremediation Strategies to Bioremediate Contam–inated Soils and Water," *Biology of Plant–Microbe Interactions*, International Society for Molecular Plant–Microbe Interactions, pp. 527–532 (1996).

Selifonova et al., "Bioluminescent sensors for detection of bioavailable Hg(II) in the environment," *Appl Environ Microbiol.* Sep. 1993;59(9):3083–90.

Shao et al., "Cloning and expression of the s–triazine hydrolase gene (trza) from rhodococcus corallinus and development of rhodococcus recombinant strains capable of dealkylating and dechlorinating the herbicide atrazine," *J Bacter.* Oct. 1995:177(20): 5748–5755.

Shao et al., "Cloning of the genes for degradation of the herbicides EPTC (S–ethyl dipropylthiocarbamate) and atrazine from Rhodococcus sp. Strain TE1," *Appl Environ Microbiol.* May 1995;61(5);2061–2065.

Smith et al., "Prediction of the persistence of the triazine herbicides atrazine, cyanazine, and metribuzine in Regina heavy clay," *Can J Soil Sci.* 1989;69:587–95.

Strong et al., "Field–scale bioremediation of atrazine–contaminated soil," American Society for Microbiology 1999 General Meeting, May 30–Jun. 3, 1999, 1 page.

Strong et al., "Field–scale remediation of atrazine–contaminated soil using recombinant *Escherichia coli* expressing atrazine chlorohydrolase," *Environ Microbiol.* Feb. 2000; 2(1):91–8.

Struthers et al., "Biodegradation of atrazine by *Agrobacterium radiobacter* J14a and use of this strain in bioremediation of contaminated soil," *Appl Environ Microbiol.* Sep. 1998;64(9):3368–75.

Tatusova et al., "BLAST 2 Sequences, a new tool for comparing protein and nucleotide sequences," *FEMS Microbiol Lett.* May 15, 1999;174(2):247–50.

Viera et al., "The pUC plasmids, an M13mp7–derived system for insertion mutagenesis and sequencing with synthetic universal primers," *Gene.* Oct. 1982;19(3):259–68.

Wenk et al., "Rapid atrazine mineralisation in soil slurry and moist soil by inoculation of an atrazine–degrading Pseudomonas sp. strain," *Appl Microbiol Biotechnol.* May 1998; 49(5):624–30.

Winkelmann et al., "Degradation and bound residue formation of atrazine in a western Tennessee soil," *Enviorn. Toxicol. Chem.* 1991;10:335–345.

Yanze–Kontchou et al., "Mineralization of the herbicide atrazine as a carbon source by a Pseudomonas strain," *Appl Environ Microbiol.* 1994;60:4297–4302.

* cited by examiner

```
   1 ctcgggtaac ttcttgagcg cggccacagc agccttgatc atgaaggcga gcatggtgac
  61 cttgacgccg ctctttttcgt tctctttgtt gaactgcacg cgaaaggctt ccaggtcggt
 121 gatgtccgcg tcgtcgtggt tggtgacgtg cgggatgacc acccagttgc ggtgcaggtt
 181 tttcgatggc ataatatctg cgttgcgacg tgtaacacac tattggagac atatcatgca
 241 aacgctcagc atccagcacg gtaccctcgt cacgatggat cagtaccgca gagtccttgg
 301 ggatagctgg gttcacgtgc aggatggacg gatcgtcgcg ctcggagtgc acgccgagtc
 361 ggtgcctccg ccagcggatc gggtgatcga tgcacgcggc aaggtcgtgt acccggttt
 421 catcaatgcc cacacccatg tgaaccagat cctcctgcgc ggagggccct cgcacgggcg
 481 tcaattctat gactggctgt tcaacgttgt gtatccggga caaaaggcga tgagaccgga
 541 ggacgtagcg gtggcggtga ggttgtattg tgcggaagct gtgcgcagcg gattacgac
 601 gatcaacgaa aacgccgatt cggccatcta cccaggcaac atcgaggccg cgatggcggt
 661 ctatggtgag gtgggtgtga ggtcgtcta cgcccgcatg ttctttgatc ggatggacgg
 721 gcgcattcaa gggtatgtgg acgccttgaa ggctcgctct ccccaagtcg aactgtgctc
 781 gatcatggag gaaacggctg tggccaaaga tcggatcaca gccctgtcag atcagtatca
 841 tggcacggca ggaggtcgta tatcagtttg gcccgctcct gccactacca cggcggtgac
 901 agttgaagga atgcgatggg cacaagcctt cgcccgtgat cgggcggtaa tgtggacgct
 961 tcacatggcg gagagcgatc atgatgagcg gattcatggg atgagtcccg ccgagtacat
1021 ggagtgttac ggactcttgg atgagcgtct gcaggtcgcg cattgcgtgt actttgaccg
1081 gaaggatgtt cggctgctgc accgccacaa tgtgaaggtc gcgtcgcagg ttgtgagcaa
1141 tgcctacctc ggctcagggg tggcccccgt gccagagatg gtggagcgcg gcatggccgt
1201 gggcattgga acagataacg gaatagtaa tgactccgta aacatgatcg gagacatgaa
1261 gtttatggcc catattcacc gcgcggtgca tcgggatgcg gacgtgctga ccccagagaa
1321 gattcttgaa atggcgacga tcgatggggc gcgttcgttg gaatggacc acgagattgg
1381 ttccatcgaa accggcaagc gcgcggacct tatcctgctt gacctgcgtc accctcagac
1441 gactcctcac catcatttgg cggccacgat cgtgtttcag gcttacgca atgaggtgga
1501 cactgtcctg attgacggaa acgttgtgat ggagaaccgc cgcttgagct tcttcccc
1561 tgaacgtgag ttggcgttcc ttgaggaagc gcagagccgc gccacagcta ttttgcagcg
1621 ggcgaacatg gtggctaacc cagcttggcg cagcctctag gaaatgacgc cgttgctgca
1681 tccgccgccc cttgaggaaa tcgctgccat cttggcgcgg ctcggattgg ggggcggaca
1741 tgaccttgat ggatacagaa ttgccatgaa tgcggcactt ccgtccttcg ctcgtgtgga
1801 atcgttggta ggtgagggtc gactgcgggc gccagcttcc cgaagaggtg aaaggcccga
1861 g
```

Fig. 8A

```
  1 mqtlsiqhgt lvtmdqyrrv lgdswvhvqd grivalgvha esvpppadrv idargkvvlp
 61 gfinahthvn qillrggpsh grqfydwlfn vvypgqkamr pedvavavrl ycaeavrsgi
121 ttinenadsa iypgnieaam avygevgvrv vyarmffdrm dgriqgyvda lkarspqvel
181 csimeetava kdritalsdq yhgtaggris vwpapattta vtvegmrwaq afardravmw
241 tlhmaesdhd erihgmspae ymecygllde rlqvahcvyf drkdvrllhr hnvkvasqvv
301 snaylgsgva pvpemvergm avgigtdngn sndsvnmigd mkfmahihra vhrdadvltp
361 ekilematid garslgmdhe igsietgkra dlilldlrhp qttphhhlaa tivfqaygne
421 vdtvlidgnv vmenrrlsfl pperelafle eaqsratail qranmvanpa wrsl
```

Fig. 8B

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: PRIMER

<400> SEQUENCE: 1
ccatgtgaac cagatcct                                                    18

<210> SEQ ID NO 2
<211> LENGTH: 18
<212> TYPE: DNA
<213> ORGANISM: Artificial Sequence
<220> FEATURE:
<223> OTHER INFORMATION: PRIMER

<400> SEQUENCE: 2
tgaagcgtcc acattacc                                                    18

<210> SEQ ID NO 3
<211> LENGTH: 1861
<212> TYPE: DNA
<213> ORGANISM: PSEUDOMONAS AERUGINOSA

<400> SEQUENCE: 3
ctcgggtaac ttcttgagcg cggccacagc agccttgatc atgaaggcga gcatggtgac        60
cttgacgccg ctcttttcgt tctctttgtt gaactgcacg cgaaaggctt ccaggtcggt       120
```

-continued

```
gatgtccgcg tcgtcgtggt tggtgacgtg cgggatgacc acccagttgc ggtgcaggtt     180
tttcgatggc ataatatctg cgttgcgacg tgtaacacac tattggagac atatcatgca     240
aacgctcagc atccagcacg gtaccctcgt cacgatggat cagtaccgca gagtccttgg     300
ggatagctgg gttcacgtgc aggatggacg gatcgtcgcg ctcggagtgc acgccgagtc     360
ggtgcctccg ccagcggatc gggtgatcga tgcacgcggc aaggtcgtgt tacccggttt     420
catcaatgcc cacacccatg tgaaccagat cctcctgcgc ggagggccct cgcacgggcg     480
tcaattctat gactggctgt tcaacgttgt gtatccggga caaaaggcga tgagaccgga     540
ggacgtagcg gtggcggtga ggttgtattg tgcggaagct gtgcgcagcg ggattacgac     600
gatcaacgaa aacgccgatt cggccatcta cccaggcaac atcgaggccg cgatggcggt     660
ctatggtgag gtgggtgtga gggtcgtcta cgcccgcatg ttctttgatc ggatggacgg     720
gcgcattcaa gggtatgtgg acgccttgaa ggctcgctct ccccaagtcg aactgtgctc     780
gatcatggag gaaacggctg tggccaaaga tcggatcaca gccctgtcag atcagtatca     840
tggcacggca ggaggtcgta tatcagtttg gcccgctcct gccactacca cggcggtgac     900
agttgaagga atgcgatggg cacaagcctt cgcccgtgat cgggcggtaa tgtggacgct     960
tcacatggcg gagagcgatc atgatgagcg gattcatggg atgagtcccg ccgagtacat    1020
ggagtgttac ggactcttgg atgagcgtct gcaggtcgcg cattgcgtgt actttgaccg    1080
gaaggatgtt cggctgctgc accgccacaa tgtgaaggtc gcgtcgcagg ttgtgagcaa    1140
tgcctacctc ggctcagggg tggcccccgt gccagagatg gtggagcgcg gcatggccgt    1200
gggcattgga acagataacg gaatagtaa tgactccgta aacatgatcg gagacatgaa    1260
gtttatggcc catattcacc gcgcggtgca tcgggatgcg gacgtgctga ccccagagaa    1320
gattcttgaa atggcgacga tcgatggggc gcgttcgttg ggaatggacc acgagattgg    1380
ttccatcgaa accggcaagc gcgcggacct tatcctgctt gacctgcgtc accctcagac    1440
gactcctcac catcatttgg cggccacgat cgtgtttcag gcttacggca atgaggtgga    1500
cactgtcctg attgacggaa acgttgtgat ggagaaccgc cgcttgagct tcttccccc    1560 tgaacgtgag ttggcgttcc ttgaggaagc gcagagccgc gccacagcta ttttgcagcg    1620
ggcgaacatg gtggctaacc cagcttggcg cagcctctag gaaatgacgc cgttgctgca    1680
tccgccgccc cttgaggaaa tcgctgccat cttggcgcgg ctcggattgg ggggcggaca    1740
tgaccttgat ggatacagaa ttgccatgaa tgcggcactt ccgtccttcg ctcgtgtgga    1800
atcgttggta ggtgagggtc gactgcgggc gccagcttcc cgaagaggtg aaaggcccga    1860
g                                                                   1861
```

<210> SEQ ID NO 4
<211> LENGTH: 474
<212> TYPE: PRT
<213> ORGANISM: PSEUDOMONAS AERUGINOSA

<400> SEQUENCE: 4

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60
```

```
Ala His Thr His Val Asn Gln Ile Leu Leu Arg Gly Gly Pro Ser His
 65                  70                  75                  80

Gly Arg Gln Phe Tyr Asp Trp Leu Phe Asn Val Val Tyr Pro Gly Gln
                 85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
370                 375                 380

Glu Thr Gly Lys Arg Ala Asp Leu Ile Leu Leu Asp Leu Arg His Pro
385                 390                 395                 400

Gln Thr Thr Pro His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu
465                 470
```

MICROBES AND METHODS FOR REMEDIATION

CONTINUING APPLICATION DATA

This application claims the benefit of U.S. Provisional Application Ser. No. 60/178,345, filed Jan. 25, 2000, which is incorporated by reference herein.

GOVERNMENT FUNDING

The present invention was made with government support under Grant No. 1434-HQ-96-GR-02678, awarded by the United States Department of the Interior. The Government has certain rights in this invention.

BACKGROUND

Commercial practices have resulted in the production of pollutants that can contaminate the environment. For instance, modem agricultural practices rely heavily on the use of herbicides to control weed populations. S-triazine (i.e., symetric triazine) herbicides, primarily atrazine and simazine, are widely used herbicides for selective control of broadleaf weeds and some grasses in a variety of crops. Since atrazine and other s-triazine herbicides biodegrade relatively slowly in soils, label directions for the use of atrazine restrict the types of crops that can be planted to prevent carryover problems in the next growing season. For example, alfalfa and soybeans are susceptible to atrazine concentrations in soil ranging from 0.09 mg/Kg to 0.53 mg/Kg, depending on the concentration of soil organic matter.

Numerous studies on the environmental fate of atrazine have shown that atrazine is a moderately persistant compound that is transformed to $CO_2$ very slowly, if at all, under aerobic or anaerobic conditions. It has a water solubility of 33 mg/l at 27° C. Its half-life (i.e., time required for half of the original concentration to dissipate) can vary from about 4 weeks to about 57 weeks when present at a low concentration (i.e., less than about 2 parts per million (ppm)) in soil. High concentrations of atrazine, such as those occurring in spill sites, have been reported to dissipate even more slowly.

As a result of its widespread use, atrazine is sometimes detected in water in concentrations exceeding the maximum contaminant level (MCL) of 3 $\mu$g/l (i.e., 3 parts per billion (ppb)), a regulatory level that took effect in 1992. Point source spills of atrazine have resulted in levels as high as 25 ppb in some wells. Levels of up to 40,000 mg/l (i.e., 40,000 ppm) atrazine have been found in the soil at spill sites more than ten years after the spill incident. Point source spills and subsequent runoff can result in the presence of atrazine in surface, subsurface, and ground water.

Atrazine removal from the soil environment can occur by several different mechanisms. At typical soil pH, atrazine is only very slowly chemically hydrolyzed (half life of 200 days) to produce hydroxyatrazine. A more significant degradation mechanism for atrazine in soils is microbial metabolism. Microbial degradation of atrazine has been demonstrated to occur via dealkylation, deamination, or dechlorination reactions.

For decontamination purposes, the most efficient method of transforming a contaminant into a less-harmful end product is by biostimulation or bioaugmentation (Liu et al. (1993) *Trends Biotechnol.,* 11 344–352). Biostimulation involves supplementing the contaminated soils to change the physical state of the contaminant, thereby converting it to a bioavailable form, or supplying a nutritional supplement or co-substrate to increase the population of indigenous bacteria capable of catabolizing the contaminant. Bioaugmentation involves inoculating soils with a non-indigenous microorganism capable of catabolizing the contaminant.

The ability of introduced live cultures of atrazine-degrading bacteria to increase biodegradation has been investigated in laboratory studies. In studies done with non-sterile soil, the success of bioaugmentation was inversely related to population levels of indigenous atrazine-degrading microorganisms (Radosevich et. al., (1996) *Biodeg.,* 7, 137–149; Struthers et al., (1998) *Appl. Environ. Microbiol.,* 64, 3368–3375; and Kontchou et al., (1993) Proceedings of the 9th Symposium on Pesticide Chemistry, Piacenza Italy. p. 533–536. Istituto di Chimica Agraria et Ambientale, Universita Cattolica del Sacro Cuore). In sterile soils devoid of indigenous atrazine degrading bacteria, it has been reported that atrazine concentration was reduced 70% (from 20 ppm to 6 ppm) in 30 days (Fadullon et al., (1998) *Environ. Sci. Health,* B33, 37–49), or eliminated from 15 ppm in 5 days (Wenk et al, (1998) *Appl. Mibrobiol. Biotechnol.,* 49, 624–630).

SUMMARY OF THE INVENTION

In view of the occasional prevalence of compounds, for instance herbicides, in the environment at levels above regulatory standards, and the long periods of time that can be required to allow natural degradation to occur, there is a need in the art for rapid methods to remediate, e.g., remove, pollutants present in the environment. The present invention represents an advance in the art of remediating compounds, for instance pollutants, in the environment. Typically, when a population of microbes expressing an enzyme activity of interest is exposed to conditions that result in 100% killing of the population, there is generally a substantial decrease in the amount of enzymatic activity retained by the cells when compared to the cells before killing. As described herein, when a population of microbes containing a hydrolase were incubated in a phosphate buffer and exposed to conditions that result in 100% killing, there was an unexpected high degree of hydrolase activity retained by the microbes when compared to the microbes before killing. When $Na_2B_4O_7$—HCl was used as a buffer instead of phosphate, the level of hydrolase activity retained by the microbes compared to the microbes before killing was unexpectedly increased to an even greater degree than observed when the phosphate buffer was used. Also unexpected was the long term stability of the killed cells. For instance, after storage at room temperature for about seven months, killed microbes retained about 50% of enzyme activity of the enzyme activity that was present in the microbes before killing.

The present invention provides a method for remediating a compound in a sample. The method includes providing at least one killed microbe that contains a polynucleotide including a coding region encoding a polypeptide, for instance a hydrolase, that degrades a compound. The coding region can be an exogenous coding region. The microbe can be, for instance, *E. coli* or *Pseudomonas aeruginosa.*

The method also includes contacting the sample that contains the compound with the at least one microbe under conditions effective to decrease the concentration of the compound in the sample relative to the concentration of the compound in a sample not contacted with the at least one microbe. The method can also include measuring the concentration of the compound in the sample after contacting the sample with the at least one microbe. The compound can be detoxified. The microbe can be killed with a cross-linking agent, for instance, glutaraldehyde, formalin, or iodine.

A sample that can be used in the methods of the present invention can include soil, water, or a combination thereof. The compound to be degraded can be at least one s-triazine, including for instance atrazine, desethylatrazine, deisopropylatrazine, desethylhydroxyatrazine, desisopropylhydroxyatrazine, desethyldesisopropylatrazine, simazine, terbuthylazine, melamine, ammelide, ammeline, prometryn, ametryn, propazine, cyanuric acid, terbutryn, cyanazine, propazine, simatone, and cyromazine.

The complement of the nucleotide sequence of a coding region useful in the present invention can include those that hybridize to the nucleotide sequence set forth at nucleotides 236 to 1660 of SEQ ID NO:3 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS. The nucleotide sequence of the coding region can be nucleotides 236 to 1660 of SEQ ID NO:3. The amino acid sequence of the polypeptide can be the amino acid sequence of SEQ ID NO:4, or an active analog or active fragment thereof.

The invention also provides a method for degrading an s-triazine in a sample, including providing at least one cross-linked microbe that contains a polynucleotide including a coding region encoding a hydrolase that degrades an s-triazine. The method also includes contacting a sample that includes the compound with the microbe under conditions effective to decrease the concentration of the compound in the sample relative to the concentration of the compound in a sample not contacted with the at least one microbe. The microbe can be a prokaryote, including, for instance, *E. coli* and *P. aeruginosa*. Less than about 40% of individual microbes can be cross-linked to each other.

In another aspect, the invention also provides at least one cross-linked microbe containing a polynucleotide that includes a coding region encoding a polypeptide that degrades at least one s-triazine.

Definitions

"Microbe" and "micro-organism" are used interchangeably herein and refer to a single-cell eukaryotic or prokaryotic organism. A microbe is "isolated" when it has been removed from its natural environment and can be grown as a pure culture. An individual microbe is a microbe that is not cross-linked to another microbe.

"Bioremediation" and "remediation" as used herein refer to decreasing the concentration of at least one compound in a sample. A sample can include, for instance, soil, a liquid, or both. The sample can be remediated while present in the environment, or remediated before being introduced to the environment. The concentration of a compound can be decreased by degrading the compound.

Water as used herein includes surface water, subsurface water, and ground water. "Surface water" is water that is standing (e.g., a puddle) or moving (e.g., a stream) above ground level. "Subsurface water" is water present in soil and above the ground water. Subsurface water includes water that entered the soil as rain and water that originated from, for instance, a nearby waterway. "Ground water" is water that is located below the subsurface water and often supplies wells and springs.

A "compound" as used herein refers to a molecule that is not typically in the environment, for instance a pollutant or a contaminant. A compound can be toxic to a plant or an animal.

"S-triazines" and "s-triazine containing compounds" are used interchangeably and refer to a type of compound. Examples of s-triazines include, for example, atrazine (2-chloro-4-ethlyamino-6-isopropylamino-1,3,5-s-triazine), desethylatrazine (2-chloro-4-amino-6-isopropylamino-s-triazine), deisopropylatrazine (2-chloro-4-ethylamino-6-amino-s-triazine), desethylhydroxyatrazine (2-hydroxy-4-amino-6-isopropylamino-s-triazine), desisopropylhydroxyatrazine (2-hydroxy-4-amino-6-isopropylamino-s-triazine), desethyldesisopropylatrazine (2-chloro-4,6-diamino-s-triazine), simazine (2-chloro-4,6-diethylamino-s-triazine), terbuthylazine (2-chloro-4-ethylamino-6-terbutylamino-s-triazine), melamine (2,4,6-triamino-s-triazine), ammelide (2,4-dihydroxy-6-amino-s-triazine), ammeline (2-hydroxy-4,6,-diamino-s-triazine), prometrym (N,N'-bis(1-methylethyl)-6-(methylthio)-1,3,5-triazine-2,4 diamine), ametryn (N-ethyl-N'-(1-methylethyl)-6-(methylthio)-1,3,5-triazine-2,4 diamine), propazine (6-chloro-N,N'-bis(1-methylethyl)-1,3,5-triazine-2,4-diamine), cyanuric acid (trihydroxy-1,3,5-triazine), terbutryn (N-(1,1-dimethylethyl)-N'-ethyl-6-(methylthio)-1,3,5-triazine-2,4-diamine), cyanazine (2-((4-chloro-6-(ethylamino)-1,3,5-triazine-2-yl)amino)-2-methylpropionitrile), propazine (6-chloro-N,N'-bis(1-methylethyl)-1,3,5-triazine-2,4-diamine), simatone (methoxy-4,6-bis(ethylamino)-s-triazine), and cyromazine (2-Cyclopropylamino-4,6-diamino-s-triazine).

"Degradation" of a compound includes, for instance, removing or otherwise changing at least a portion of the compound. Degradation of a toxic compound can result in a compound having increased toxicity relative to the undegraded compound, a compound having about the same toxicity as the undegraded compound, or a compound having lower toxicity relative to the undegraded compound. A degraded compound having lower toxicity to a plant and/or an animal relative to the undegraded compound is referred to herein as detoxified.

"Killed" as used herein refers to a microbe that has been rendered incapable of reproducing and does not respire.

"Cross-linking agent" as used herein refers to a chemical that, when exposed to a sample containing molecules, causes the formation of bonds between the molecules. The bonds can be, for instance, covalent, ionic, or hydrogen, preferably covalent. Exposure of a microbe to a cross-linking agent can result in the cross-linking of molecules within the microbe, and optionally the cross-linking of microbes. Cross-linking agents include agents that catalyze cross-linking but are not included in the resulting cross-linked molecule as well as agents that are included in the resulting cross-linked molecule.

"Hydrolase" as used herein is a polypeptide that catalyzes hydrolysis, i.e., a chemical reaction in which water reacts with another molecule to form two or more new molecules. This involves the splitting of the molecule hydrolyzed. Non-limiting examples of hydrolases include phosphotriesterase, chlorohydrolases (for instance atrazine chlorohydrolase), nitrilases (for instance aliphatic nitrilase), and β-galactosidase.

"Polynucleotide" as used herein refers to a polymeric form of nucleotides of any length, either ribonucleotides or deoxynucleotides, and includes both double- and single-stranded DNA and RNA. A polynucleotide may include both coding and non-coding regions, and can be obtained directly from a natural source (e.g., a microbe), or can be prepared with the aid of recombinant, enzymatic, or chemical techniques. A polynucleotide can be linear or circular in topology. A polynucleotide can be, for example, a portion of a vector, such as an expression or cloning vector, or a fragment.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

"Coding region" refers to a polynucleotide that encodes a polypeptide, usually via mRNA, when placed under the control of appropriate regulatory sequences. The boundaries of the coding region are generally determined by a translation start codon at its 5' end and a translation stop codon at its 3' end. "Exogenous coding region" refers to a foreign coding region, i.e., a coding region that is not normally present in a microbe, or a coding region that is normally present in a microbe but is operably linked to a regulatory region to which it is not normally operably linked.

"Regulatory region" refers to a polynucleotide that regulates expression of a coding region to which a regulatory region is operably linked. Non-limiting examples of regulatory regions include promoters, enhancers, transcription initiation sites, translation start sites, translation stop sites, and terminators.

"Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region.

The term "complement" and "complementary" as used herein, refers to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The terms complement and complementary also encompass two polynucleotides where one polynucleotide contains at least one nucleotide that will not base pair to at least one nucleotide present on a second polynucleotide. For instance the third nucleotide of each of the two polynucleotides 5'-ATTGC and 5'-GCTAT will not base pair, but these two polynucleotides are complementary as defined herein. Typically two polynucleotides are complementary if they hybridize under certain conditions.

As used herein, "hybridizes," "hybridizing," and "hybridization" means that a single stranded polynucleotide forms a noncovalent interaction with a complementary polynucleotide under certain conditions, as described herein.

"Support" as used herein refers to a matrix, for instance a filter, to which a microbe can be attached.

Unless otherwise specified, "a," "an," "the," and "at least one" are used interchangeably and mean one or more than one.

BRIEF DESCRIPTION OF THE FIGURES

FIG. 8: (A) The nucleotide sequence available at Genbank Accession Number U55933 (SEQ ID NO:3), and (B) the amino acid sequence available at GenBank Accession Number AAC64663 (SEQ ID NO:4).

DETAILED DESCRIPTION OF THE INVENTION

Figure 1:
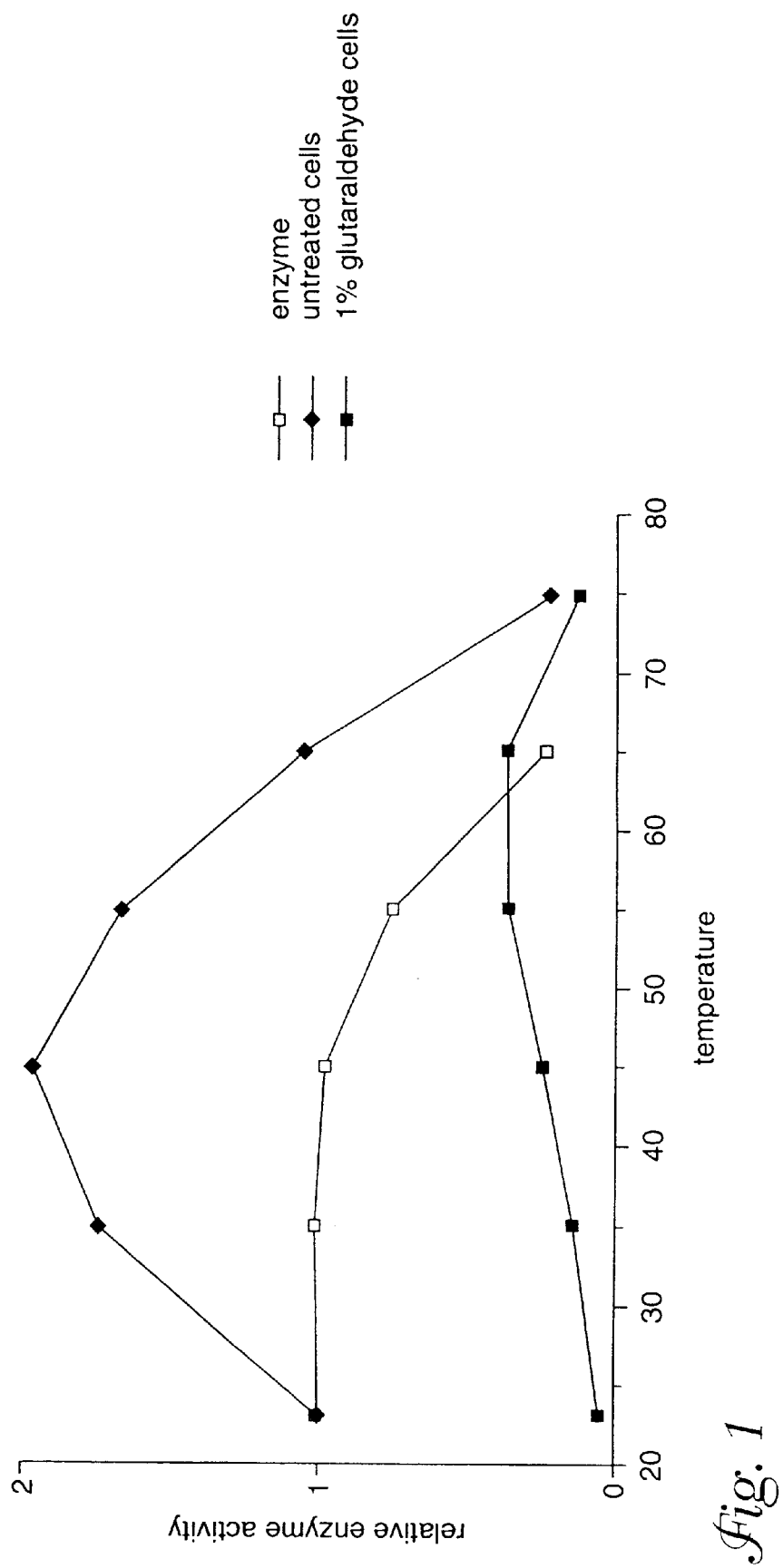
FIG. 1: Temperature stability of cross-linked enzyme activity. Enzyme, purified AtzA; untreated cells, cells not exposed to glutaraldehyde; 1% glutaraldehyde cells, cells exposed to glutaraldehyde.

An aspect of the present invention is directed to methods for the remediation of a compound in a sample. The sample is contacted with at least one killed microbe under conditions effective to decrease the concentration of the compound. Optionally, the concentration of the compound is measured after the sample is contacted with a killed microbe. The microbe includes a polynucleotide that contains a coding region encoding a polypeptide. The polypeptide is able to degrade, preferably detoxify, the compound. Preferably, the compound is at least one s-triazine.

Important applications of the present invention include, but are not limited to, decreasing the concentration of a compound in a sample by degrading, preferably detoxifying, a compound present in the environment. An advantage of preferred aspects of the invention is the use of microbes as a catalyst to remediate a sample. Typically, the use of living microbes containing recombinant DNA in the environment requires regulatory approval. However, the use of killed microbes (whether recombinant or not) typically does not require regulatory approval, and therefore can be done without spending time and resources to acquire approval before the killed microbe is used in the methods of the present invention. It is expected that the use of killed microbes is more likely to be accepted by the public.

Typically, a sample is from a terrestrial environment or an aquatic environment, for instance from soil, water, or a combination thereof. Alternatively, a sample can be, for instance, a mixture containing the compound to be degraded. A non-limiting example of a mixture is a herbicide, either liquid or solid, before it is applied to a field. While not intending to be limiting, it is believed that the methods of the present invention will decrease the concentration of compounds, preferably at least one s-triazine, in the environment including surface water and subsurface water and also prevent compounds from moving into ground water. Thus, preferred aspects of the present invention can be used to decrease the amount of compounds, preferably at least one s-triazine, which can occur in drinking water.

Another advantage of certain aspects of the present invention is retention of the ability of the polypeptide to degrade, preferably detoxify, a compound. This retention of the ability to degrade is also referred to herein as "stability." Consequently, the polypeptide's ability to degrade the compound has a longer shelf life, will remain at a high level of activity for a longer time while in contact with the sample containing the compound, and will be more stable in use at higher temperatures or more extreme pH.

Compounds

Typically, compounds degraded, preferably detoxified, in the methods of the present invention include compounds that are not typically in the environment, e.g., pollutants or contaminants. For instance, the compound can be present in the environment due to application of the compound to, for example, a field. Alternatively, the compound can be present in the environment due to the accidental release of a quantity of the compound, for example, a spill. Non-limiting examples of compounds include herbicides and pesticides, preferably herbicides, more preferably, an s-triazine-containing compound. The types of compounds that can be degraded using the methods of the present invention is not a limiting aspect of the invention.

The methods of the present invention result in a decrease in the concentration of the compound in the sample relative to the concentration of the compound in the sample not contacted with the microbe. The method used to measure a compound's concentration in a sample varies with the type of compound, and is known to a person of ordinary skill in the art. Typically, an amount of a sample is extracted with a solvent in which the compound is soluble. The concentration of the compound in the solvent is then determined using a method that detects the compound. For instance, gas chromatography can be used to measure atrazine concentration.

Preferably, the methods of the present invention result in the detoxification of the compound in the sample. The method used to measure the toxicity of a compound varies with the type of compound. In general, the measurement of the toxicity of a compound is known to a person of ordinary skill in the art.

A non-limiting example of a compound that can be remediated is an s-triazine-containing compound that includes a chlorine atom and at least one alkylamino side chain. Such compounds have the following general formula:

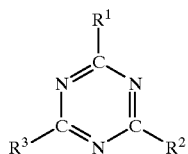

wherein $R^1$=Cl, $R^2$=$NR^4R^5$ (wherein $R^4$ and $R^5$ are each independently H or a $C_{1-3}$ alkyl group), and $R^3$=$NR^6R^7$ (wherein $R^6$ and $R^7$ are each independently H or a $C_{1-3}$ alkyl group), with the proviso that at least one of $R^2$ or $R^3$ is an alkylamino group. As used herein, an "alkylamino" group refers to an amine side chain with one or two alkyl groups attached to the nitrogen atom. Examples of such compounds include atrazine (2-chloro-4-ethlyamino-6-isopropylamino-1,3,5-s-triazine), desethylatrazine (2-chloro-4-amino-6-isopropylamino-s-triazine), deisopropylatrazine (2-chloro-4-ethylamino-6-amino-s-triazine), desethylhydroxyatrazine (2-hydroxy-4-amino-6-isopropylamino-s-triazine), desisopropylhydroxyatrazine (2-hydroxy-4-amino-6-isopropylamino-s-triazine), desethyldesisopropylatrazine (2-chloro-4,6-diamino-s-triazine), simazine (2-chloro-4,6-diethylamino-s-triazine), terbuthylazine (2-chloro-4-ethylamino-6-terbutylamino-s-triazine), melamine (2,4,6-triamino-s-triazine), ammelide (2,4-dihydroxy-6-amino-s-triazine), ammeline (2-hydroxy-4,6,-diamino-s-triazine), prometryn (N,N'-bis(1-methylethyl)-6-(methylthio)-1,3,5-triazine-2,4 diamine), ametryn (N-ethyl-N'-(1-methylethyl)-6-(methylthio)-1,3,5-triazine-2,4 diamine), and propazine (6-chloro-N,N'-bis(1-methylethyl)-1,3,5-triazine-2,4-diamine).

Other non-limiting examples of compounds that can be remediated include nerve gas agents such as sarin, phosphodiesters, 2,4-dichlorophenoxyacetic acid, 2,4,5-trichlorophenoxyacetic acid, halogenated hydrocarbons such as dichloromethane, glyphosate, and 1,1,1-trichloro-2, 2-bis-(4-chlorophenyl)ethane.

Microbes

A microbe used in the methods of the present invention can be colonial several-celled eukaryotic or prokaryotic micro-organism containing less than about 100 cells, or a single-cell eukaryotic or prokaryotic micro-organism. An example of a colonial several-celled micro-organism is the cyanobacteria Nostoc spp. Preferably, the microbe is a single-cell prokaryotic micro-organism, more preferably a gram negative prokaryote micro-organism. Examples of useful gram-negative prokaryotic microbes include *E. coli,* Pseudomonas species such as *P. aeruginosa,* Salmonella species such as *S. typhimurium,* Klebsiella species, Enterobacter species, Erwinia species, or Serratia species. Preferably the gram-negative prokaryotic microbe is *E. coli.* The microbe expresses a polypeptide that degrades, preferably detoxifies, a compound. The polypeptide can be present in the cytoplasm or present on the surface of the microbe. The polypeptide can be normally expressed by the microbe, i.e., the microbe is non-recombinant, or the polypeptide can be expressed by a coding region that has been introduced to the microbe, i.e., the microbe is recombinant. Preferably, the microbe is recombinant. Without intending to be limiting, it is expected that recombinant microbes can be made to express a polypeptide useful in the present methods at a higher level than a microbe that normally expresses the polypeptide.

A polynucleotide encoding a polypeptide useful in the methods of the present invention can be inserted in a vector. Construction of vectors containing a polynucleotide of the invention employs standard ligation techniques known in the art. See, e.g., Sambrook et al, *Molecular Cloning: A Laboratory Manual.,* Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli.* Preferably the vector is a plasmid. A vector containing a polynucleotide encoding a polypeptide useful in the methods of the present invention can be introduced to a microbe using methods known to the art. The appropriate method to use varies depending on the type of microbe, and include, for instance, $CaCl_2$ mediated transformation, electroporation, and transduction.

An expression vector optionally includes regulatory regions operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Typically, a promoter results in greater expression of the operably linked coding region when compared to expression of the coding region when operably linked to its natural promoter. Preferred promoters for bacterial transformation include lac, lacUV5, tac, trc, T7, SP6 and ara.

An expression vector can optionally include a Shine Dalgarno site (e.g., a ribosome binding site), and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., (1981) *J. Mol. Biol.* 148 107–127).

Optionally, the vector includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

Killing

A microbe used in the methods of the present invention can be killed by exposure to a cross-linking agent. Useful cross-linking agents are typically able to penetrate the cell membrane, cross-link the polypeptide that causes the degradation of a compound, and kill the microbe. Optionally, more than one cross-linking agent can be used. Examples of cross-linking agents include aldehyde compounds (for instance glutaraldehyde, formaldehyde, glyoxal, and dialdehyde starch), 1,5-difluoro-2,4-dinotro-benzene, diazobenzidine, tannic acid, trimethylolpropane trimethacrylate, $(NH_4)_3ZrOH(CO_3)_3$, bifunctional maleimides, (for instance N,N'-(1,3-phenylene) bismaleimide), diisocyanates (for instance hexamethylenediisocyanate), bisphenylazides (for instance bis-[β-(4-azidosalicylamido)ethyl]disulfide), photocrosslinkable resins, iodine and formalin. Alternatively, it is expected that a microbe can be killed by exposure to other agents, including for instance those disclosed in U.S. Pat. No. 4,695,455 (Barnes et al.).

The conditions used to kill the microbe result in killing of most, preferably all, of the microbes present. These conditions typically result in a decrease in the total enzymatic activity of the polypeptide that causes degradation of a compound; however, the remaining enzymatic activity is typically more stable. For instance, the enzyme activity of the killed microbe is maintained at higher temperatures for longer periods of time compared to the living microbe or the purified enzyme, or the enzyme activity of the killed microbe is maintained for a longer period of time compared to the living microbe or the purified enzyme. Preferably, at least about 90%, more preferably at least about 95%, most preferably greater than 95% of the enzymatic activity remains after incubation of killed cells at 37° C. for about 16 hours when compared to killed cells incubated at 23° C. for the same period. Preferably, at least about 60%, more preferably at least about 80%, most preferably at least about 95% of the enzymatic activity remains after incubation of killed cells at 45° C. for about 16 hours when compared to killed cells incubated at 23° C. for the same period. Preferably, at least about 60%, more preferably at least about 80%, most preferably at least about 92% of the enzymatic activity remains after incubation of killed cells at 55° C. for about 16 hours when compared to killed cells incubated at 23° C. for the same period.

The long term stability of the enzyme activity remaining in the killed microbes is surprisingly high. Typically, killed microbes are stored in liquid suspension at room temperature in a buffer at a pH of about 6.5 to about 7.5, preferably about pH 7. Generally, the liquid contains a solute at a concentration sufficient to decrease, preferably prevent, the growth of contaminating microbes. Useful solutes are those that do not destabilize the enzyme. An example of a solute that could destabilize includes, for instance, sodium chloride. Non-limiting examples of solutes that can be used include glycerol, preferably at about 50% vol/vol, potassium sulfate, and ammonium sulfate. Preferably, after seven months of storage at room temperature, killed microbes retain about 50% of the enzyme activity of the enzyme activity that was present in the microbes before killing Typically, a microbe expressing a polypeptide that causes the degradation of a compound is exposed to an agent, preferably a cross-linking agent, such that a high degree of killing results and the decrease in the total enzymatic activity is minimized. The degree of killing can be determined by measuring the number of colony forming units after exposure and comparing to the number of colony forming units of the microbe that has not been exposed to the cross-linking agent. The amount of enzymatic activity after exposure to a cross-linking agent can be determined by measuring the enzymatic activity present after exposure and comparing to the enzymatic activity of the microbe that has not been exposed to the cross-linking agent.

The microbe expressing the appropriate polypeptide can be grown in liquid media or on solid media, preferably liquid media, and then exposed to the agent, preferably a cross-linking agent. Typically, the microbe is in liquid suspension when exposed to the cross-linking agent. The growth phase of the microbe can impact the stability of the enzyme activity of the killed microbe. In general, enzymatic activity in microbes is typically more stable in microbes grown to stationary phase, but cells are easier to kill in exponential phase. Accordingly, a population of microbes are typically grown to exponential phase or stationary phase and exposed to varying concentrations of a cross-linking agent. The population of microbes exposed to the concentration of cross-linker that results in 100% killing is then tested for enzymatic activity. The stability and the amount of the enzymatic activity remaining after killing the microbes can be optimized by varying the conditions used to kill the microbes. For instance, the concentration of salt in the solution can be varied. Different types of buffer can also be used, including for instance sodium phosphate or $Na_2B_4O_7$—HCl, preferably $Na_2B_4O_7$—HCl. Without intending to be limited by theory, it is believed that the Na$_2$B$_4$O$_7$—HCl interacts with carbohydrates present on the outer surface of the microbes and prevents clumping of the cells, thereby allowing better diffusion of the cross-linking agent into the cells to result in better killing and increased retention of enzyme activity in the killed microbes compared to the microbes not exposed to the cross-linking agent. Preferably, when 100% of the microbes present in a population exposed to a cross-linking agent are killed, the killed microbes retain at least about 30%, more preferably at least about 50%, most preferably at least about 65% of the enzymatic activity that was present in the microbes before killing.

The concentration of the microbe, e.g., the number of colony forming units per unit volume, can also be varied. Typically, when using a cross-linking agent, increasing the concentration of the microbe can result in not only the cross-linking of molecules within a microbe, but can also result in the cross-linking of individual microbes to each other. Microbes are typically cross-linked to each other by the cross-linking of polypeptides present on the cell surface of the microbes. Whether individual microbes are cross-linked to each other or not can be easily determined by viewing microbes under a microscope after exposure to a cross-linking agent; the presence of clumped microbes indicates that individual microbes are cross-linked to each other. In increasing order of preference, less than about 40%, less than about 20%, less than about 10%, most preferably less than about 1% of individual microbes are cross-linked to each other.

Polypeptides and Polynucleotides

Microbes used in the methods of the present invention typically include a polypeptide that causes the degradation, preferably detoxification, of a compound. Preferably, a polypeptide is a hydrolase. Without intending to be limiting, it is expected that hydrolases are more likely to retain the ability to degrade, preferably detoxify, a compound after exposure of the hydrolase to a cross-linking agent. In contrast, it is expected that mono-oxygenases (for instance ammonia mono-oxygenase) and dioxygenases (for instance toluene dioxygenase) will be more likely to be inactivated by exposure to a cross-linking agent. Non-limiting examples of hydrolases include phosphotriesterase and chlorohydrolases (for instance atrazine chlorohydrolase), and other hydrolases, such as aliphatic hydrolase, epoxide hydrolase, and β-galactosidase.

Preferably, the hydrolase is atrazine chlorohydrolase. As used herein, the coding region encoding a polypeptide capable of dechlorinating atrazine and originally identified in Pseudomonas sp. strain ADP, ATCC No. 55464 (U.S. Pat. No. 5,508,193, Mandelbaum) and expressed in *E. coli* is referred to as "atzA." atzA can be referred to in the art as the atzA structural gene. The polypeptide encoded by atzA is referred to as "AtzA." Examples of the cloned wild-type nucleotide coding region and the amino acid sequence derived from the nucleotide sequence of the coding region are provided as nucleotides 236 to 1660 of the nucleotides of SEQ ID NO:3, and the amino acid sequence of SEQ ID NO:4. The terms atrazine chlorohydrolase polypeptide, atrazine chlorohydrolase enzyme, atrazine chlorohydrolase, atrazine halidohydrolase enzyme, or simply AtzA, are used interchangeably, and refer to an atrazine chlorohydrolase enzyme involved in the degradation of atrazine and similar molecules as discussed herein.

Polypeptides useful in some aspects of the invention include those having a significant level of similarity with the amino acid sequence of SEQ ID NO:4. The similarity is referred to as structural similarity and is generally determined by aligning the residues of the two amino acid sequences (i.e., a candidate amino acid sequence and the amino acid sequence of SEQ ID NO:4) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in the amino acid sequence of SEQ ID NO:4. A candidate amino acid sequence can be isolated from a microbe, or can be artificially constructed by using, for instance, recombinant techniques, or chemically or enzymatically synthesized. Preferably, two amino acid sequences are compared using the Blastp program, version 2.0.9, of the BLAST 2 search algorithm, as described by Tatusova, et al. (FEMS *Microbiol Lett* 1999, 174:247–250), and available at ncbi.nlm.nih.gov/gorf/b12.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." Preferably, a polypeptide includes an amino acid sequence having a structural similarity with the amino acid sequence of SEQ ID NO:4 of greater than 70% identity, more preferably at least about 80% identity, most preferably at least about 90% identity.

Alternatively, individual microorganisms can be screened for the presence of polypeptides that degrade, preferably detoxify, a compound. The expression by a microorganism of a polypeptide useful in the methods of the invention can be assayed by, for instance, the ability of the microorganism to reproduce in the presence of the compound, for instance at least one s-triazine, or by measurement of degradation of the compound, for instance at least one s-triazine. Other examples of polypeptides encoded by the coding regions of this invention include those that can be isolated from other organisms (see Wackett et al., U.S. patent application Ser. No. 08/546,793).

Additional examples of polypeptides encoded by the coding regions of this invention include artificially constructed coding regions. For instance, gene shuffling, also termed recursive sequence recombination, has been used to construct coding regions encoding polypeptides that have similarity with the wild-type AtzA of SEQ ID NO:4. The construction of coding regions encoding polypeptides that impart resistance to an s-triazine is described in Wackett et al., U.S. application Ser. No. 09/155,036. Typically, artificially constructed coding regions encode a polypeptide having a specific activity that is at least about the same as the wild-type polypeptide. Preferably, the specific activity of the polypeptide encoded by the artificially constructed coding region is at least about 2 times faster than the wild-type polypeptide, more preferably at least about 5 times faster, most preferably at least about 10 times faster than the wild-type polypeptide.

The polypeptides useful in some aspects of the invention include a polypeptide having SEQ ID NO:4, or an active analog or active fragment of SEQ ID NO:4. An active analog or active fragment of a polypeptide having SEQ ID NO:4 is one that is expressed by a microbe and is able to degrade, preferably detoxify, at least one s-triazine. Active analogs of a polypeptide having SEQ ID NO:4 include polypeptides having amino acid substitutions that do not eliminate the ability to degrade at least one s-triazine. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Active fragments of a polypeptide having SEQ ID NO:4 include a portion of the polypeptide containing deletions or additions of one or more contiguous or noncontiguous amino acids such that the resulting polypeptide will degrade at least one s-triazine. Active analogs and active fragments of polypeptides of SEQ ID NO:4 will degrade at least one s-triazine.

Alternatively, a polypeptide useful in some aspects of the invention is encoded by a polynucleotide, the complement of which hybridizes to nucleotides 236 to 1660 of SEQ ID NO:3 under conditions of low stringency, preferably high stringency.

Polynucleotides encoding polypeptides useful in some aspects of the invention include those having a significant level of similarity with the nucleotides of the coding region of SEQ ID NO:3. The similarity is referred to as structural similarity and is determined by aligning the residues of the two polynucleotides (i.e., the nucleotide sequence of the candidate coding region and the nucleotide sequence of the coding region of SEQ ID NO:3) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to a coding region present in SEQ ID NO:3 (i.e., nucleotides 236–1660 of SEQ ID NO:3). Preferably, two nucleotide sequences are compared using the Blastn program, version 2.0.9, of the BLAST 2 search algorithm, as described by Tatusova, et al. (FEMS *Microbiol Lett* 1999, 174:247–250), and available at ncbi .nlm.nih.gov/gorf/b12.html. Preferably, the default values for all BLAST 2 search parameters are used, including reward for match=1, penalty for mismatch=–2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with the coding region of SEQ ID NO:3 of at least about 85%, more preferably at least about 90%, even more preferably at least about 95%, most preferably at least about 99% identity.

Individual wild-type microorganisms can be screened for the presence of nucleotide sequences that are similar to nucleotides 236 to 1660 of SEQ ID NO:3. Screening methods include, for instance, hybridization of polynucleotides immobilized on a membrane with a detectably labeled probe. Standard hybridizing conditions use hybridization buffer (250 mM $Na_2HPO_4$, pH 7.4, 2 ml/liter 0.5 M EDTA, pH 8.0, 10 grams/liter bovine serum albumin) containing 25 nanograms labeled probe DNA/ml hybridization buffer. Hybridization is allowed to occur at 65° C. for at least 4 hours. For low stringency hybridizations, the membrane is washed at 65° C., three times for twenty minutes each in a solution containing 2×SSC (1×SSC: 150 mM NaCl, 15 mM sodium citrate, pH 7.0) and 0.1% SDS. For high stringency hybridizations, the membrane is washed at 65° C., three times for twenty minutes each in a solution containing 0.1×SSC and 0.1% SDS. Preferably, a probe will hybridize to the nucleotide sequence set forth at nucleotides 236 to 1660 of SEQ ID NO:3 under the high stringency conditions. Generally the probe does not have to be complementary to all the nucleotides of a polynucleotide as long as there is hybridization under the conditions described herein.

Preferred probes for identifying polynucleotides encoding a polypeptide that degrades at least one s-triazine are polynucleotides complementary to a coding region of the invention. For instance, a probe can comprise a consecutive series of nucleotides complementary to a portion of nucleotides 236 to 1660 of GenBank accession number U55933. A probe is typically no greater than about 1,400 bases and no less than about 10 bases. Typically a probe does not hybridize under conditions described herein with nucleotides that are not part of a coding region of the present invention. A particularly preferred probe is the approximately 600 base ApaI-PstI fragment that can be obtained from the plasmid pMD4 (de Souza et al., *Applied Environ. Microbiol.*, 61, 3373–3378 (1995)). Methods of detectably labeling a probe are known to the art. The polynucleotide that is identified by the probe is further analyzed using methods known to one of ordinary skill in the art to determine if it encodes a polypeptide imparting resistance to at least one s-triazine. Another method for screening individual microorganisms for the presence of nucleotide sequences that are similar to the coding regions of the present invention is the polymerase chain reaction (PCR). For instance, the primers 5'-CCATGTGAACCAGATCCT-3'(SEQ ID NO: 1) and 5'-TGAAGCGTCCACATTACC-3'(SEQ ID NO:2) can be used to screen individual microorganisms for the presence of nucleotide sequences that are similar to the coding regions of the present invention.

Remediation

A killed microbe that includes a polypeptide useful in the methods of the present invention can be added to a sample containing a compound to be degraded, preferably detoxified. Typically, the microbe is added directly to the sample. For instance, if the sample includes soil, amounts of soil can be removed from a contaminated site and the microbe added by mixing. The microbe can also be worked into the soil. If the sample is ground water, the microbe can be added directly to ground water, or the ground water can be removed and the microbe added. Optionally, the sample and microbe are then incubated under conditions effective to decrease the concentration of the compound.

Variables that can be altered to provide conditions to allow degradation of the compound include, for instance, pH and salt concentration. The appropriate pH and salt concentration depend on the polypeptide. Optimal pH and salt concentration can be determined by evaluating the enzymatic activity of the polypeptide at various pH and salt concentrations. Other variables that can be altered include the time the microbe and sample are incubated together and the temperature of the incubation. Typically, longer incubations of the microbe and sample result in greater amounts of compound being degraded. Typically, the microbe and sample are incubated together for at least about 24 hours, more preferably at least about 1 week, most preferably at least about 2 weeks. It is expected that polypeptides useful in the methods of the present invention will work at temperatures of at least about 0° C. The highest temperatures for incubating a microbe and a sample typically depends on the individual polypeptide. Typically, the temperature of the microbe is not so high that it inhibits the activity of the polypeptide.

Optionally, a solvent can also be added to the sample. Useful solvents solublize the compound and promote interaction between the microbe and the compound and typically result in a greater amount of degradation. Examples of solvents useful in degrading atrazine include detergents, for instance Triton X-100, or soybean oil.

The concentration of the compound to be degraded can be measured after the microbe and sample have been placed in contact. Typically, time is allowed to elapse after the sample is contacted with the microbe before the concentration of the compound in the sample is determined. The method used to measure a compound's concentration in a sample varies with the type of compound, and is known to a person of ordinary skill in the art. Typically, an amount of a sample is extracted with a solvent in which the compound is soluble. The concentration of the compound in the solvent is then determined using a method that detects the compound. For instance, gas chromatography can be used to measure atrazine concentration.

As an alternative to adding the microbe directly to the sample, the microbe can be attached to a support, and then the sample containing the compound to be degraded placed in contact with the microbe. For example, the microbe can be attached to a matrix, for instance a filter, and then a liquid containing the compound to be degraded can be run through the matrix. Examples of liquids include, for instance, drinking water, or an effluent before it is introduced to the environment. Cells can be attached by methods known to the art (see, for instance, Mosbach et al., eds., "Immobilized enzymes and cells. Part B," *Methods Enzymol.*, 135, (1987)).

The present invention is illustrated by the following examples. It is to be understood that the particular examples, materials, amounts, and procedures are to be interpreted broadly in accordance with the scope and spirit of the invention as set forth herein.

EXAMPLE 1

This example demonstrates the optimization of conditions for cross-linking cells with the cross-linking agent glutaraldehyde, and the stability of the enzymatic activity of the cross-linked cells.

Materials and Methods

Growth and Cross-linking

The bacterial strain used was *Escherichia coli* DH5α (pMD4) (de Souza, et al., *Applied and Environmental Microbiology*, 61, 3373–3378 (1995)). This has a 1.9 kb region of DNA from Pseudomonas sp. strain ADP containing the atzA gene encoding atrazine chlorohydrolase (AtzA).

*E. coli* DH5α (pMD4) was grown in 600 ml batches in 2 L flasks in LB medium with 22 µg/ml chloramphenicol with shaking at 37° C. The O.D.$_{600\ nm}$ of the culture was monitored periodically during growth and, unless noted otherwise, cells were harvested in stationary phase between 6 and 24 hours after the O.D. stopped increasing. It was important to harvest cells in stationary phase, because the AtzA enzyme activity was much more stable in cells harvested in stationary phase than in cells harvested in exponential phase. Cells were harvested by centrifugation, resuspended in buffer, pelleted again and resuspended in buffer at 4% cells (wet wt./vol.). The cell suspension was mixed with an equal volume of 0.06–0.6% (w/v) glutaraldehyde in buffer to give a final 2% cell concentration and 0.03–0.3% glutaraldehyde. The mixture was stirred for 1 hour at 23° C.

Then 1 M Tris-HCl, pH 8.8, was added to a final Tris concentration of two to three times the molar concentration of glutaraldehyde and allowed to react with excess unreacted glutaraldehyde for 1 hour. Cells were then harvested by centrifugation, washed, and resuspended in 40 mM sodium phosphate, pH 7.2. The buffer used in cross-linking was, unless noted otherwise, either 40 mM sodium phosphate, pH 7.2, or Borax (50 mM unless noted otherwise), NaCl (150 mM unless noted otherwise), adjusted to pH 9.0 with HCl.

Atrazine Degradation Assays in Aqueous Solution

Approximately 5 µl of untreated or cross-linked cell suspensions (2% wet wt./vol) were added to 1 ml 20 mM Tris-HCl, pH 7.5, 30 ppm atrazine, and incubated 1 hour at room temperature. The reaction was stopped by removing the cells by centrifugation. 800 µl of supernatant was removed, and the O.D.$_{262\ nm}$ was measured and compared to the O.D.$_{262\ nm}$ of a sample not exposed to cells. The decrease in atrazine concentration was calculated using $\epsilon_{262\ nm}=3.42$ at pH 7.5. The degradation product, hydroxyatrazine, has no absorbance at 262 nm.

Measurement of Atrazine Concentrations in Soil

Glutaraldehyde cross-linked cells (6.5% w/v suspension in 12 mM sodium phosphate) and buffer totaling 1.5 ml, including the cell suspension, were added to 5 grams of atrazine-contaminated soil with about 6,000 ppm atrazine. Samples were incubated at room temp for 7 days.

Four grams of soil was mixed with 10 ml water and 15 ml dichloromethane (DCM). The mixture was shaken vigorously for 3 minutes. Then it was centrifuged to pellet the soil and separate the aqueous and organic layers. Between 20 and 50 µl organic layer was mixed with 1 ml of HPLC grade DCM for gas chromatography.

Gas chromatography was performed using a Hewlett-Packard 6890 GC system equipped with a flame ionization detector and interfaced to an HP 79994A chemstation. The HP capillary column used was 30 meters long, 320 µm diameter, and contained a 0.25 µm film of 5% phenylmethylsiloxane. Temperature was ramped over the 15 minute run period from 50° C. to 300° C. Injection volume was 2 µl. The chromatograph was operated in a constant pressure mode at 25 psi, with constant gas composition of 30 ml/min hydrogen, 350 ml/min air and 25 ml/min of makeup gas, which was either ultra pure helium or nitrogen. Calibration standards were run with each set of samples. Atrazine retention time was 9.1 minutes with ultrapure He makeup gas or 8.9 minutes with $N_2$ makeup gas.

The quantity of atrazine in the sample was determined by the peak height as compared with standards.

Results

Table 1 shows the extent to which glutaraldehyde is able to kill the recombinant *E. coli* without complete loss of AtzA activity.

TABLE 1

Killing of E. coli (pMD4) by glutaraldehyde and relative AtzA activity of the cells after glutaraldehyde treatment. Cells were harvested, washed and resuspended in 40 mM sodium phosphate, pH 7.2, at 2% w/v cells. Glutaraldehyde was added to the indicated concentration, and reacted for 1 hour. Tris from 1 M Tris-HCl, pH 8.8, was added to 2× the molar concentration of glutaraldehyde to react with excess glutaraldehyde and reacted for 1 hour. Cells were harvested, washed, and resuspended in 40 mM sodium phosphate, pH, 7.2. 100 μl of cells at 0.2% w/v were plated on LB plates to determine survivors, and cells were assayed for atrazine degrading activity.

| % glutaraldehyde | # of colonies | relative activity |
|---|---|---|
| 0 | lawn | 100 |
| 0.003 | lawn | 96 |
| 0.01 | ~10,000 | 86 |
| 0.03 | 0 | 30 |
| 0.1 | 0 | 15 |
| 0.3 | 0 | 6.7 |

Table 2 shows that while glutaraldehyde cross-linking causes a considerable decrease in AtzA activity, the residual activity is extremely stable. There was very little loss of activity even after overnight incubation at 55° C.

TABLE 2

Heat Stability of cross-linked cells compared to untreated cells. μg atrazine degraded/min/mg cells assayed at 23° C.

|  | untreated cells | 1% glutaraldehyde cross-linked cells |
|---|---|---|
| no heat treatment | 4.95 | 0.243 |
| after 55° C. overnight | 0.45 (9%) | 0.224 (92%) |

Another way to measure temperature stability of the enzyme is to do assays at different temperatures. The results of assaying purified AtzA (purified as described by de Souza et al., *J. Bacteriol.*, 178, 4894–4900 (1996)), *E. coli* (pMD4), and *E. coli* (pMD4) cross-linked with glutaraldehyde, at various temperatures are shown in FIG. 1. Assay mixes were pre-equilibrated at the temperature, and then the reaction was started by adding the enzyme or cells. Assay was for 10 minutes and then the reactions were stopped and the change in absorbance at 262 nm was measured to measure atrazine disappearance. Untreated cells were more stable to temperature than free enzyme, and cross-linked cells were more stable still. Activity of the untreated cells peaked at 45° C. and of the cross-linked cells at 65° C.

There was a remarkable difference in the stability of the AtzA activity in whole cells harvested in stationary phase verses harvested in exponential phase. This is shown in Table 3. The activity of the cells per gram of cells was the same for the exponential and stationary phase cells; however, the activity was much more stable to heat in the stationary phase cells.

TABLE 3

Dependence of the stability of cellular AtzA activity on the growth stage of cells. Cells were harvested in exponential phase or 12 hours after reaching stationary phase and resuspened in 40 mM sodium phosphate, pH 7.2, and then treated as below, before being assayed.
Relative Activity, Assayed at 23° C.

| Pretreatment | Exponential | Stationary |
|---|---|---|
| no heat | 100 | 101 |
| 47° C., 40 min | 67 | 117 |
| 55° C., 40 min | 0 | 129 |

To reduce the loss of activity that occurred with cross-linking, different cross-linking conditions were tried. The cells retained more activity if cross-linked in borate buffer. It was not a pH effect, because cross-linking in ethanolamine or carbonate buffer at pH 8.9 did not result in an increased activity. It appeared to be a specific effect of the borate. Table 4 shows that the higher the borate concentration during cross-linking, the greater the retained activity.

TABLE 4

Effect of Borax concentration on cellular AtzA activity after cross-linking in 0.3% glutaraldehyde in $Na_2B_4O_7$—HCl, pH 8.9.

| Borax Concentration | Relative Activity |
|---|---|
| 5 mM | 1.0 |
| 20 mM | 1.26 |
| 80 mM | 1.89 |
| 200 mM | 2.16 |

Table 5 shows that the presence of 0.1 to 0.4 M NaCl in the cross-linking buffer also helps to maximize the retention of enzyme activity.

TABLE 5

Effect of salt concentration during cross-linking on subsequent AtzA activity of the cross-linked cells. Cells were cross-linked in 50 mM $Na_2B_4O_7$—HCl, pH 9.0, 0.3% glutaraldehyde, plus the indicated NaCl concentration, at 2% cells w/v.

|  | Relative Activity |
|---|---|
| untreated cells | 100 |
| cells cross-linked in 0 M NaCl | 20 |
| 0.1 M NaCl | 39 |
| 0.2 M NaCl | 40 |
| 0.4 M NaCl | 38 |
| 0.8 M NaCl | 23 |

The cross-linked cells were used to degrade atrazine in soil (Table 6). The difference between the dry cell control and the soil+100 μl cells is 8 mg of atrazine degraded per 5 gram of soil, i.e., 2 mg more than the amount degraded in the soil+buffer sample, with no cells. The 100 μl of cell suspension used here, operating at its Vmax, would have degraded 29 mg of atrazine in 7 days in liquid solution. So the degradation of atrazine is considerably slower in soil than it theoretically could be if transfer of atrazine to cells and product away from cells were not limiting.

TABLE 6

Degradation of atrazine in soil by cross-linked cells. Degradation assays in 5 grams of atrazine-contaminated soil were done with E. coli (pMD4) cross-linked with 0.3% glutaraldehyde. Cells as a 6.5% w/v suspension in 12 mM sodium phosphate were added to the soil. Buffer totalling 1.5 ml, including the cell suspension, was added to a 5 grams soil sample. Samples were incubated at room temp for 7 days.

|  | ppm atrazine (average of 3) |
|---|---|
| dry soil control | 5,130 |
| soil + buffer | 3,951 |
| soil + 4 µl cells | 4,216 |
| soil + 20 µl cells | 3,932 |
| soil + 100 µl cells | 3,568 |

In an attempt to solubilize the hydrophobic atrazine and improve its transfer to cells, soil atrazine degradations were done with Triton or soybean oil added to soil in addition to the cross-linked cells. Both the oil and the Triton did result in faster degradation (Table 7). This was not the result of oil simulating the degradation by native flora, because the degradation still depended on addition of cross-linked cells.

TABLE 7

Effect of Triton X-100 or Soybean Oil on facilitating degradation of atrazine in soil by cross-linked E. coli (pMD4). To 5 gram soil, 17 mg wet wt. of cells cros-linked with 0.3% glutaraldehyde were added in 1.5 ml total buffer which was 26 mM $K_2CO_3$. Triton (45 mg) or soybean oil (120 mg) was also added. Samples were incubated for 8 days.

|  | ppm atrazine (average of 3) |
|---|---|
| dry soil control | 5,615 |
| soil + buffer | 4,465 |
| soil, buffer, and cells | 3,387 |
| soil, buffer, cells, and oil | 2,369 |
| soil, buffer, cells, and Triton | 2,636 |

Figure 2:
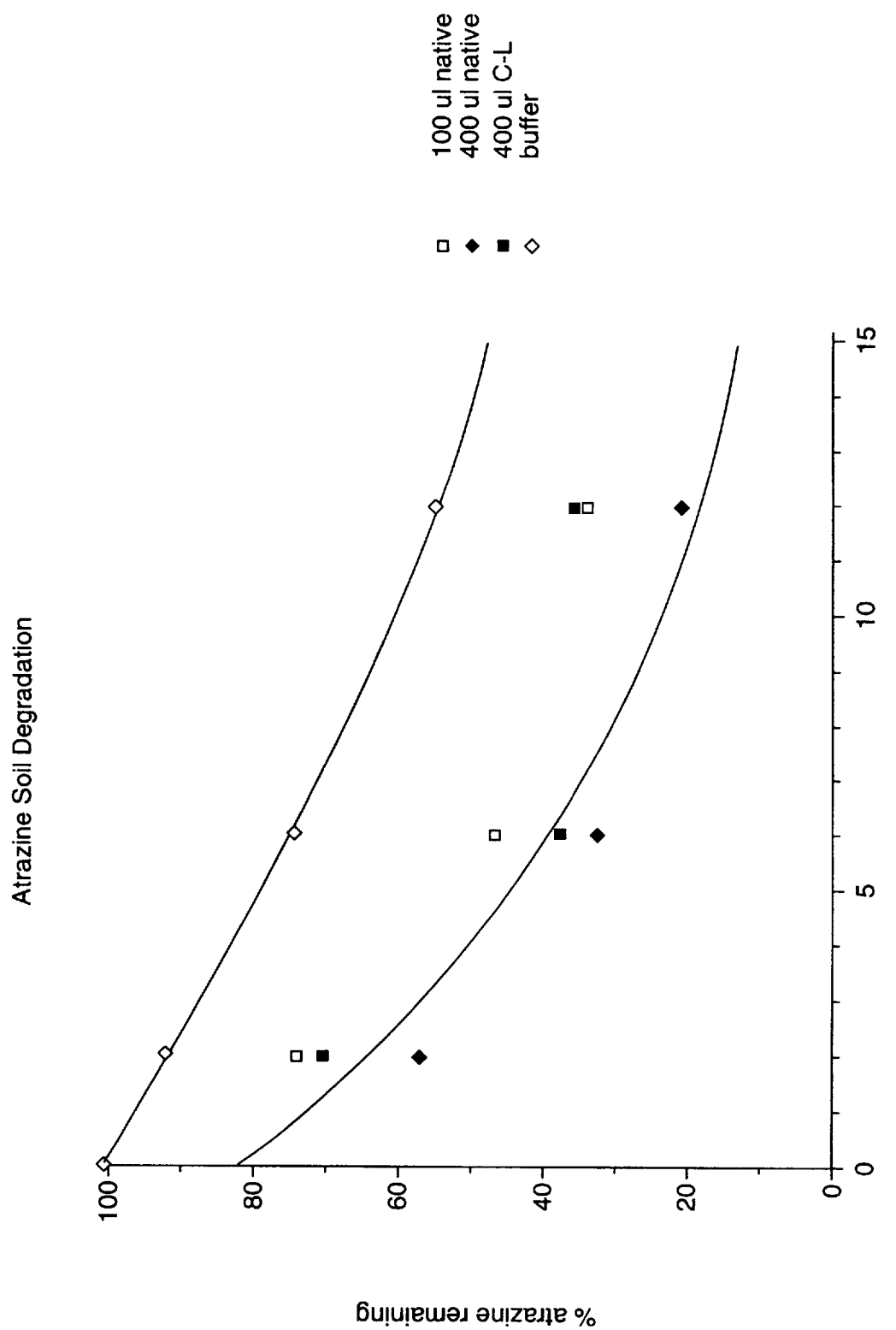
FIG. 2: Atrazine soil degradation. Native, cells not treated with cross-linking agent; C-L, cells treated with cross-linking agent.

A time course of degradation in soil with 400 µl of cross-linked cells or 100 or 400 µl of cells not treated with glutaraldehyde (native cells in FIG. 2) indicated that the rate of degradation by native cells slowed over time, but it slowed to about the same extent with cross-linked cells.

EXAMPLE 2

This example describes the first use of killed, recombinant organisms in field remediation studies in the United States. The results demonstrate the ability to effect a 77% reduction in atrazine concentration (from 6,700 ppm) in only 8 weeks by adding a suspension of stabilized, killed recombinant bacterial cells containing active atrazine chlorohydrolase.

Experimental Procedures

Chemicals: Authentic atrazine (provided by Novartis Crop Protection) was used for gas chromatography standards, and enzyme activity and plate clearing assays. HPLC grade dichloromethane used for atrazine extraction, 50% aqueous gluteraldehyde (photographic quality), Tris-base, and sodium tetraborate used in cell cross-linking were obtained from Fisher (Pittsburgh, Pa.).

Bacterial strains, plasmids, and growth conditions: Atrazine chlorohydrolase, AtzA, was produced by growing a large quantity of E. coli DH5α containing plasmid pMD4 (deSouza et al. (1995) Appl. Environ. Microbiol., 61, 3373–3378). pMD4 contains the atzA coding region, and the AtzA polypeptide that is expressed is not secreted by the E. coli. Briefly, 300 liters of cells were grown at 37° C. in a batch fermentor at 4 pounds per square inch, pH 7.0, with a stir rate of 400 rpm. Air flow was maintained at 125 standard liters per minute, with oxygen supplementation if dissolved oxygen fell below 50%. Sixty six liters of media containing 12 grams/liter tryptone, 24 grams/liter yeast extract, 1.1 grams/liter $KH_2PO_4$, 4.7 grams/liter $K_2HPO_4$, 4 grams/liter glucose and 25 mg/liter chloramphenicol was continuously fed into the reactor. Feed was controlled with a peristaltic pump, and feed rate was increased from 2 to 5 liters/hour over 14 hours.

Cross-Linking of Cells: Cells were killed and cross-linked by the addition of concentrated glutaraldehyde (i.e., 50% glutaraldehyde) to a final concenration of 0.3% gluteraldehyde. Cross-linked cells were allowed to incubate for 1 hour at 22° C. with stirring at 300 rpm. After incubation, 7.5 kg of sodium tetraborate was added to the culture and the pH was adjusted to 8.8 with the addition of $H_3PO_4$. After another hour of incubation, 1 kg of Tris-base was added and pH adjusted to 8.6 with $H_3PO_4$. The suspension was allowed to stir overnight at 22° C., then the cells were harvested by centrifugation at 15,000×g in a Sharples AS-16 centrifuge (Alpha Laval, Warminster, Pa.). Killed and cross-linked whole cells were used as enzyme carriers. To determine if the cross-linked E. coli cell suspension contained only dead cells, aliquots of the killed cell suspension were plated onto LB agar medium (Sambrook et al. (1989) *Molecular Cloning: A Laboratory Manual,* Cold Spring Harbor Laboratory Press, Cold Spring Harbor, N.Y.), and LB medium containing 500 parts per million (ppm) atrazine and 30 µg/ml chloramphenicol. The term one ppm indicates one gram of atrazine per million grams of total solution.

Enzyme activity: The kinetics of the purified AtzA enzyme have been described previously (de Souza et al. (1996) *J. Bacteriol.,* 178, 4894–4900). Enzyme velocity is the amount of substrate converted per unit time. Enzyme velocity in killed whole cells was determined by adding 10 µl of 20% (wt/vol) killed cell suspension to 1 ml of a solution of 30 ppm atrazine and 30 mM Tris HCl buffer at pH 7.5. The reaction was allowed to proceed at room temperature for approximately 1 hour, and stopped by adding 12 µl of 6 M HCl to a 0.8 ml aliquot of the mixture. Tubes containing the stopped aliquots were centrifuged for 10 minutes at 10,000× g to remove cells from the suspension.

Atrazine concentration was determined spectrophotometrically using an extinction coefficient of $\epsilon_{270\ nm}$=3.88 $mM^{-1}$ in 60 mM HCl, or $\epsilon_{262\ nm}$=3.42 $mM^{-1}$ at pH 7.0.

Enzyme activity tests were performed at 5 temperatures between 0° C. and 24° C. on three batches of cross-linked enzyme 7, 8 and 9 months after cross-linking. The 7 month old cells were the same ones used in the field remediation study, while the 8 and 9 month old cells were from separate 1 liter batch reactions. Samples were stored: 1) frozen as a 20% suspension in neutralized cross-linking media (neutralized cross-linking media is the growth medium with glutaraldehyde, sodium tetraborate, Tris-base, and $H_3PO_4$ added as described above, with the pH further adjusted to pH 7.5 with $H_3PO_4$); 2) at room temperature as a 20% suspension in neutralized cross-linking media; 3) at room temperature as a 20% suspension in 30 mM phosphate buffer pH 7.2; 4) or as a moistened cell pellet.

Figure 3:
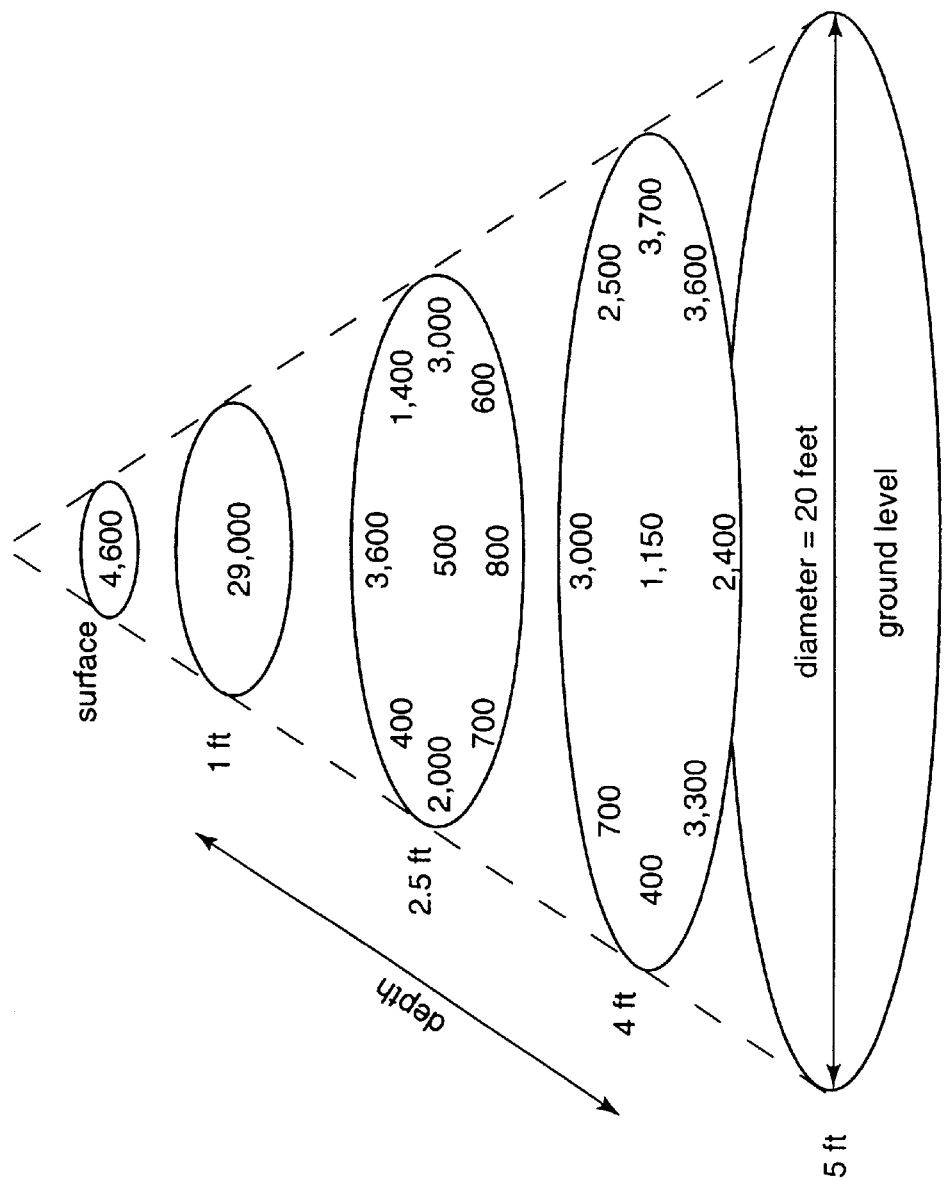
FIG. 3: Distribution of atrazine (ppm) in the 35 yd$^3$ soil excavated after an accidental spill. The values shown are from independent determinations of atrazine concentration at each test point. If atrazine were uniformly distributed, which it clearly is not, the average concentration would be 11,500 ppm, based on the known amount of atrazine spilled.

Spill site soil: The spill occurred in Spring 1997 in South Dakota when a 250 gallon tank of 4 lb/gallon atrazine suspension fell off a truck and burst open. The spill was contained by excavating and covering 35 yd³ of contaminated soil on 6 mil plastic sheeting. The distribution of atrazine in the soil was determined by taking soil samples from various locations in the excavated soil and determining the atrazine concentration in those samples by extraction with DMC and gas chromatographic analysis, as described herein. As shown in FIG. 3, distribution of atrazine in the soil after 18 months of on-site storage was non-uniform. The silty-loam soil, an Eakin-Ethan complex (USDA (1995) Soil Survey Geographic Database (SSURGO), Charles Mix County, S.D.) had 3.6% organic matter, pH 7.4, and an electrical conductivity of 5.1 mmhos/cm in a 1:1 slurry. Soil analysis was performed by the Soils Testing Laboratory at the University of Minnesota (St. Paul, Minn.). The soil was very low in phosphorous, with a Bray's P value of 1 ppm. Total nitrogen was 0.68% (6,800 ppm), and was partly due to the atrazine content itself which was estimated to add approximately 2,400 ppm nitrogen to the soil.

Atrazine degradation due to indigenous microorganisms: Bench studies were done on atrazine-contaminated soil to assess the extent to which disappearance of atrazine in this soil is the result of microbial action versus surface-catalyzed hydrolysis. A 300 gram aliquot of the spill-contaminated soil was sieved through a 2 mm screen, moistened to approximately 20% of dry weight, and divided into 6 sterile culture flasks. One set of triplicates was sterilized by autoclaving the soil for 1 hour per day at 121° C., on each of three subsequent days, after which soil moisture level was restored to 20% using sterile water. The other set of triplicates remained untreated. Soil sterility was verified at each sampling point using LB and minimal media plate assays as described below. Sterile technique was used to obtain aliquots for atrazine analysis, and atrazine levels were determined by soil extraction and gas chromatography analysis as described below.

In the 18 months that this soil was stored on-site following contamination by an accidental atrazine spill, a significant population of indigenous microorganisms capable of catabolizing atrazine developed. In laboratory experiments, atrazine levels in non-supplemented moistened soil declined 84% from 17,100 ppm to 2,700 ppm in a 5 week period. Results show that when microbial populations were killed by autoclaving, no atrazine degradation occurred and atrazine levels remained constant at 15,100 ppm.

Despite the presence of significant populations of indigenous atrazine degrading microorganisms, the ability of these bacteria to significantly reduce the atrazine concentration under field conditions appears limited. If the original atrazine was uniformly distributed in the 35 yd$^3$ of containment soil, the concentration of atrazine would average approximately 11,500 ppm. Atrazine was not uniformly distributed, however, and ranged from 400 to 29,000 ppm (FIG. 3).

Biostimulation bench-top experiments: Bench studies were performed on 45 gram aliquots of spill-contaminated soil to assess the extent to which soil supplements would stimulate microorganisms present in the soil to metabolize atrazine. This stimulation is referred to as biostimulation. First stage experiments screened 13 potential biostimulation agents shown in Table 8. Efficacy of the supplements was evaluated by comparing the decline in atrazine 19 days after addition of the supplement to 45 grams of soil.

TABLE 8

Influence of soil supplements on degradation of atrazine in spill-site soil.

| | Supplement | % degradation |
|---|---|---|
| 1 | 0.5 ml soybean oil | 42 |
| 2 | 1 ml soybean oil<br>1 ml: 0.1% Na-citrate + 0.1% | 12 |

TABLE 8-continued

Influence of soil supplements on degradation of atrazine in spill-site soil.

| | Supplement | % degradation |
|---|---|---|
| 3 | glucose<br>2 ml: 0.1% Na-citrate + 0.1% | 21 |
| 4 | glucose | 48 |
| 5 | 1 ml glycerol | 36 |
| 6 | 2 ml glycerol | 16 |
| 7 | 1 ml non-fat whey | 37 |
| 8 | 2 ml non-fat whey | 27 |
| 9 | 1 g ground corn | 33 |
| 10 | 2 g ground corn | 39 |
| 11 | buffer only | 43 |
| 12 | water only, no buffer | 26 |
| 13 | no supplement | 11 |

This experiment was followed by a three factor central composite statistical experiment (Box et al. (1978) *Statistics for Experimenters: An Introduction to Design, Data Analysis, and Model Building.* John Wiley and Sons, Washington D.C.) designed to simultaneously and rigorously test the effects of multiple experimental parameters on atrazine degradation. This experimental method is a sub-set of factoral statistical designs that, when coupled with multiple regression analysis to calculate the response surface, allows quantitative optimization of parameter levels. Three variables (carbon concentration, phosphate concentration, and soil pH) were chosen for testing based on the results of the first stage experiments, combined with previous results showing that pH affects atrazine degradation rate (Mattan C. (1998) *Dechlorination of Atrazine by the Enzyme atrazine Chlorohydrolase During Simulated Water Treatment Processes.* Masters Thesis, University of Minnesota). Carbon (present as a 50:50 mixture of dextrose:citrate) was added to soil in the range of 0–25,000 ppm (0–1.16 grams carbon per 45 grams soil), phosphate was added in the range of 0–600 ppm, as 12 mM sodium phosphate buffer, and change in soil pH was attempted by adjusting the pH of the added phosphate buffer in the range 6.5–8.5. Sixteen samples in 2 blocks were augmented as shown in Table 9. Results were analyzed for significance using the MacAnova statistical software package developed at the University of Minnesota (available at ftp://umnstat.stat.umn.edu/pub/macanova.

TABLE 9

Experimental design to simultaneously analyze effects of soil modifications on atrazine degradation. Initial atrazine concentration was 4,500 ppm. Multiple regression of the results show that carbon addition reduces atrazine degradation (p-value = 0.002), and phosphorus addition increases atrazine degradation (p-value = 0.03).

| | pH | Carbon (grams/45 grams soil) | Phosphorus (ppm) | Final concentration of atrazine, (ppm) |
|---|---|---|---|---|
| block 1 | | | | |
| 1 | 7 | 0.08 | 150 | 1,370 |
| 2 | 8 | 0.08 | 150 | 1,970 |
| 3 | 7 | 0.8 | 150 | 1,705 |
| 4 | 8 | 0.8 | 150 | 1,350 |
| 5 | 7 | 0.08 | 450 | 2,280 |
| 6 | 8 | 0.08 | 450 | 1,090 |
| 7 | 7 | 0.8 | 450 | 3,515 |
| 8 | 8 | 0.8 | 450 | 1,870 |
| block 2 | | | | |
| 9 | 7.5 | 0.44 | 300 | 1,840 |

TABLE 9-continued

Experimental design to simultaneously analyze effects of soil modifications on atrazine degradation. Initial atrazine concentration was 4,500 ppm. Multiple regression of the results show that carbon addition reduces atrazine degradation (p-value = 0.002), and phosphorus addition increases atrazine degradation (p-value = 0.03).

| | pH | Carbon (grams/45 grams soil) | Phosphorus (ppm) | Final concentration of atrazine, (ppm) |
|---|---|---|---|---|
| 10 | 7.5 | 0.44 | 300 | 1,320 |
| 11 | 6.5 | 0.44 | 300 | 1,420 |
| 12 | 8.5 | 0.44 | 300 | 1,475 |
| 13 | 7.5 | 0 | 300 | 900 |
| 14 | 7.5 | 1.16 | 300 | 1,910 |
| 15 | 7.5 | 0.44 | 0 | 2,540 |
| 16 | 7.5 | 0.44 | 600 | 1,730 |

Experimental protocol at spill site: Selection of field scale treatment protocols was guided by the results of the initial laboratory scale experiments. Four treatment protocols were set-up in triplicate, as shown in Table 10. Treatments consisted of: 1) 1 yd$^3$ control plots containing only moistened soil; 2) 1 yd$^3$ biostimulation plots augmented with 300 ppm phosphate in the form of triple superphosphate fertilizer (A. H. Hoffman, Inc., Landisville, Pa.); 3) 0.5 yd$^3$ plots receiving AtzA enzyme in the form of 0.5% (w/w) killed recombinant E. coli cells (the addition of the killed cells is referred to as bioaugmentation), and 4) 0.5 yd$^3$ plots receiving a combination of phosphate plus 0.5% (w/w) killed recombinant E. coli cells. A Bobcat skid loader was used to separate nine yd$^3$ of the most highly contaminated portions of soil from the total volume of 35 cubic yards contaminated with atrazine. This portion was homogenized using the Bobcat skid loader by repeatedly mixing and combining the soil on a large tarp. Nine-1 yd$^3$ treatment bins (1 foot×4 foot×8 foot), constructed from ½" plywood lined with 6 mil polyethylene, were designed to fully contain contaminated soil and treatments.

TABLE 10

Treatments used in field scale bioremediation studies.

| | treatment protocol |
|---|---|
| control | moistened soil |
| biostimulation | 300 ppm phosphorus (triple super phosphate) |
| bioaugmentation | 0.5% (w/w) killed cross-linked recombinant cells |
| combination | 300 ppm phosphorus + 0.5% cells |

Sampling: Individual samples consisted of 50 ml volumes of soil taken from multiple places within each treatment plot. Samples were obtained in triplicate from each treatment plot, resulting in 9 individual data points at each time point for each of the 4 treatment protocols. Time points for sample acquisition were time 0 (Sep. 22, 1998), 1 week (Sep. 30, 1998), 4 weeks (Oct. 21, 1998), 8.5 weeks (Nov. 21, 1998), and 12 weeks (Dec. 16, 1998). Samples were immediately frozen on dry ice and shipped overnight to the University of Minnesota for analysis. On receipt, samples were stored at −15° C. until analysis could be performed.

Analytical Methods

Plate assays: Modified R-minimal medium (Eaton et al. (1982) J. Bacteriol., 151, 48–57; Selifonova O. et al. (1993) Appl. Environ. Microbiol., 59, 3083–3090) plates containing 500 ppm atrazine as the sole nitrogen source were used to determine if atrazine metabolizing microorganisms were present in the spill-contaminated soil. The suspension of small atrazine particles in the clear agar causes these plates to be opaque. A zone of clearing surrounding the colonies indicated degradation of atrazine by bacteria (deSouza et al. (1995) Appl. Environ. Microbiol., 61, 3373–3378). Plates used to grow recombinant strains contained 30 µg/ml chloramphenicol.

Atrazine extraction: Aliquots of soil weighing between 5 and 10 grams were taken from the homogenized soil samples for atrazine analysis, and remainder of the sample was refrozen at −15° C. Atrazine concentration was assessed using a simplified procedure based on a methanol (MeOH) extraction procedure for determining parts per billion (ppb) concentrations of atrazine in soil (Koskinen et al. (1991) Soil Sci. Soc. Am. J., 55 561–562). The soil aliquots were shaken at 250 rpm with 20 ml water and 25 ml dichloromethane (DCM) for a minimum of 2 hours on a reciprocating shaker. Tubes were centrifuged at 3,000 rpm for 15 minutes. The DCM layer was pipetted into a glass vial and dried by adding a small amount of anhydrous sodium sulfate. Between 20 µl and 50 µl of the DCM layer was added to 1 ml of HPLC grade DCM for gas chromatography. Final dilutions for each sample were individually calculated. Accuracy of the simplified procedure was tested by comparing the atrazine extracted from homogenized soil samples using the MeOH extraction procedure (Koskinen et al. (1991) Soil Sci. Soc. Am. J., 55, 561–562) to that extracted from the same samples using the simplified procedure (n=72). At high atrazine concentrations (greater than 1,400 ppm), the two extraction techniques produced statistically similar results (p-value= 0.9).

Gas chromatography: Gas chromatography was performed using a 6890 GC system (Hewlett-Packard, Palo Alto, Calif.) equipped with a flame ionization detector and interfaced to an HP 79994A chemstation. The HP capillary column used was 30 meters long, 320 µm in diameter, and contained a 0.25 µm film of 5% phenyl methyl siloxane. Temperature was ramped over the 15 minute run period from 50° C. to 300° C. Injection volume was 2 µl. The chromatograph was operated in a constant pressure mode at 25 psi, with constant gas composition of 30 ml/minute hydrogen, 350 ml/minute air, and 25 ml/min of makeup gas which was either ultra pure helium or nitrogen. Calibration standards were run with each set of samples. Atrazine retention time was 9.1 minutes with ultra pure helium makeup gas or 8.9 minutes with nitrogen makeup gas.

Soil temperature: The soil temperature at 4 inches depth was obtained from the Chamberlain-National Weather Service reporting station #a391619, elevation 1,465 feet, latitude 43.73N and longitude 99.32W. This weather station is less than 40 miles from the spill site, elevation 1,612.

Statistical analysis: Data were tested for statistical significance using the analysis of variance package included in Microsoft Excel 98.

Results

Enzyme activity: Viability tests of the killed cell suspension showed no cell growth on solid LB or solid LB plus atrazine and chloramphenical. Cross-linking to kill cells resulted in some enzyme inactivation; immediately after cross-linking, killed cells retained 65% enzyme activity as compared to the live cell activity. The A270 in the suspension containing 30 ppm atrazine and killed cells dropped 0.25 absorption units in 55 minutes, corresponding to an AtzA enzyme velocity of 167 mg/day/g cross-linked cells.

Cross-linked cell suspensions retain significant enzyme activity over long storage time, if stored properly. Suspensions stored at room temperature for 7 months retained only 24% of their original enzyme activity if stored in complex media, but retained 55% of the original enzyme activity if stored in pH 7 phosphate buffer. After 8 and 9 months of storage in pH 7 phosphate buffer, cross-linked cells retained 51% and 41% of original enzyme activity, respectively. Cross-linked cells that were frozen showed no enzyme activity after 7 months.

Temperature dependence of whole-cell activity: Kinetics of atrazine degradation in soil as the result of treatment with cross-linked cell suspension are temperature dependent (FIG. 3). In the first week of treatment, the soil temperature averaged 19° C. and atrazine level dropped 57%. In the next 4 weeks, the soil temperature averaged 13° C. and the atrazine level declined an additional 40%. Degradation dropped to 25% over the next 4.5 weeks when the soil temperature was 7° C., and stopped altogether at a soil temperature of 4° C.

Laboratory experiments: Soil from the atrazine spill site that was plated directly onto minimal media augmented with 500 ppm atrazine as a nitrogen source supported bacterial growth. This confirmed the existence of microbes in the soil whose capability for catabolizing atrazine might be enhanced by biostimulation.

First stage screening of potential biostimulation agents indicated that atrazine degradation in this soil appeared most influenced by phosphate buffer and perhaps simple sugars. Further testing of the effects of pH, carbon addition, and phosphate addition on atrazine degradation was implemented using a statistically designed central composite experiment. These results are shown in Table 9. Carbon addition decreased atrazine degradation (p-value=0.002), and phosphorus addition increased atrazine degradation (p-value=0.03). The effect of pH manipulation was statistically insignificant. Optimal atrazine degradation occurred at 300 ppm phosphorus addition. These results were used to construct the four field-site treatment protocols as described above.

Figure 4:
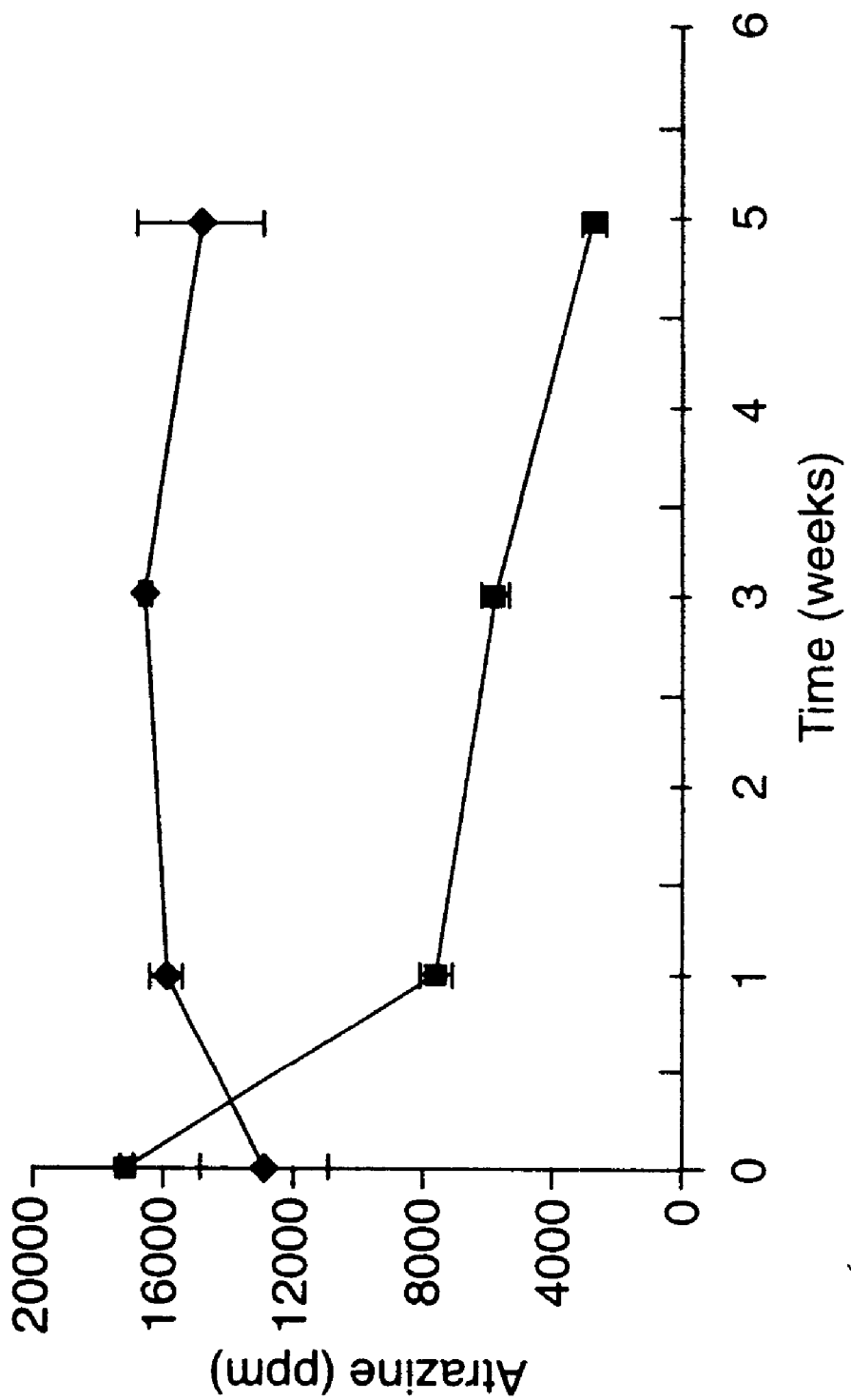
FIG. 4: Microbial degradation of atrazine in bench test studies. Sterilized soil, (♦); non-sterilized soil, (■), Error bars represent 1 standard deviation.

Microbial mechanism for atrazine degradation: Results of atrazine degradation studies done in soil are shown in FIG. 4. In unsterilized soil, the atrazine concentration declined 84% from 17,100 ppm to 2,700 ppm over the 5 week sampling period. The first order reaction rate constant was 0.08/day ($R^2$=0.95). This is well within the 0.01–0.2/day range of rate constants for atrazine mineralization in soil under laboratory conditions measured by Radosevich et. al. ((1996) *Biodeg.*, 7, 137–149). In sterilized soil, no atrazine degradation occurred, and atrazine concentration remained constant at 15,100 ppm. The sterilized soil remained sterile for the length of the experiment, as determined by plating assays. This strongly indicates that microorganisms are responsible for atrazine degradation in soil, and is consistent with other reports in the literature (Jones et al. (1982) *J. Environ. Qual.*, 11, 632–638; Smith et al. (1989) *Can. J. Soil Sci.*, 69, 587–595; and Winkelmann et al. (1991) *Environ. Toxicol. Chem.*, 10, 335–345).

Figure 5A:
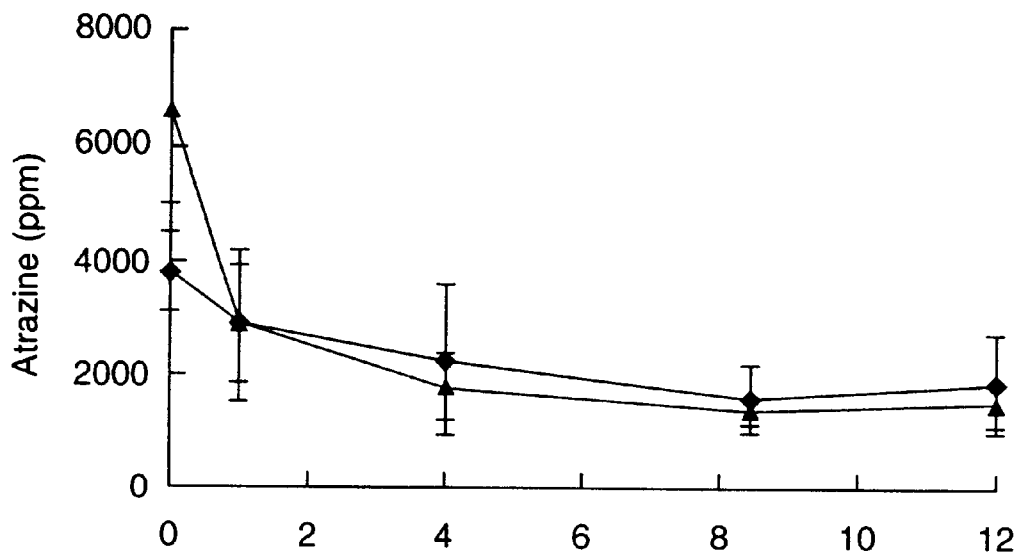
FIG. 5: Atrazine biodegradation in field test plots. A. Bioaugmentation (♦), (0.5% killed recombinant E. coli cells) and biostimulation plus bioaugmentation (▲) plots (0.5% killed recombinant E. coli cells plus 300 ppm phosphate). B. Control (●), and biostimulation (■) (300 ppm phosphate) plots. Error bars represent 1 standard deviation.
Figure 5B:
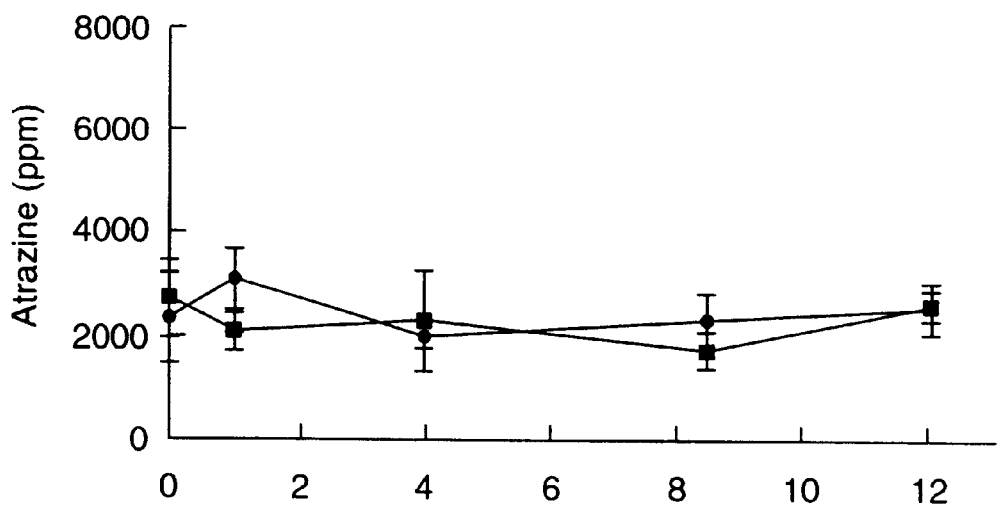
Figure 6:
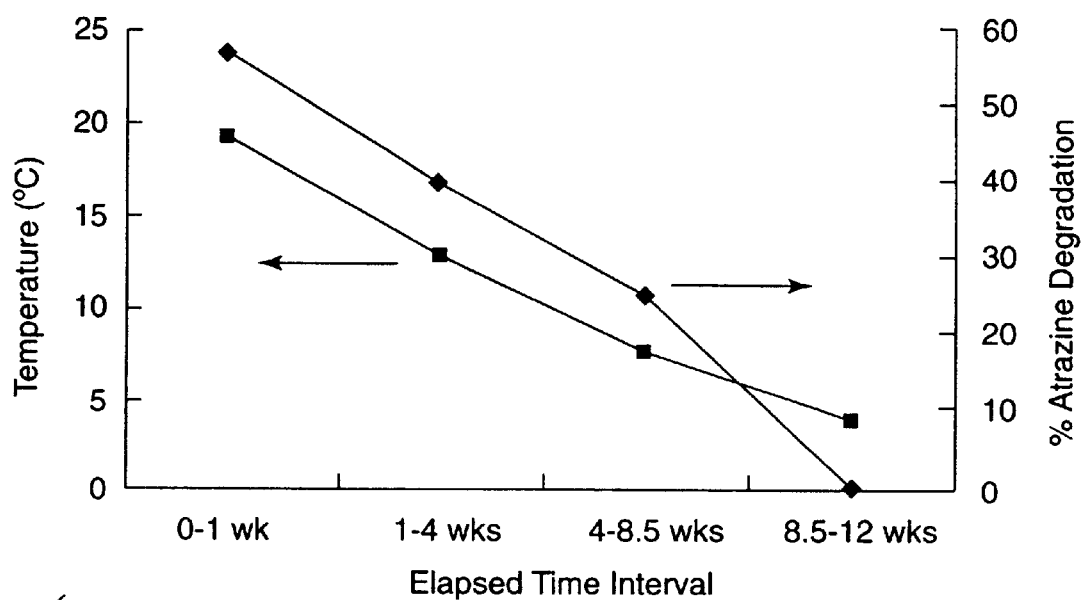
FIG. 6: The influence of soil temperature on atrazine degradation. Atrazine degradation in combination treatment plots (♦) and soil temperature at 4 inches depth (■) as a function of elapsed time in the field experiment.

Field studies: Atrazine concentration as a function of elapsed time in the field test plots is presented in FIG. 5. After 12 weeks, atrazine levels in plots containing atrazine degrading enzyme in the form of 0.5% killed recombinant E. coli cells, atrazine levels declined by 53% from 3,800 ppm to 1,800 ppm (this is statistically significant at p-value= 0.16). In plots augmented with the combination of phosphate and killed recombinant cells, atrazine degradation was 77%, with levels declining from 6,700 ppm to 1,450 ppm (significant at p-value=0.03). In contrast, plots not treated with enzyme (the control plots and plots augmented with 300 ppm phosphate) exhibited no significant degradation (p-values of 0.43 and 0.73, respectively), and atrazine concentration remained at its initial average of 2,500 ppm. Temperatures in the soil are presented in FIG. 6. Significant degradation in the test plots continued until the soil temperature dropped below 7° C. This analysis shows that no significant degradation occurred during this time period when the soil temperature averaged 3.6° C.

Figure 7:
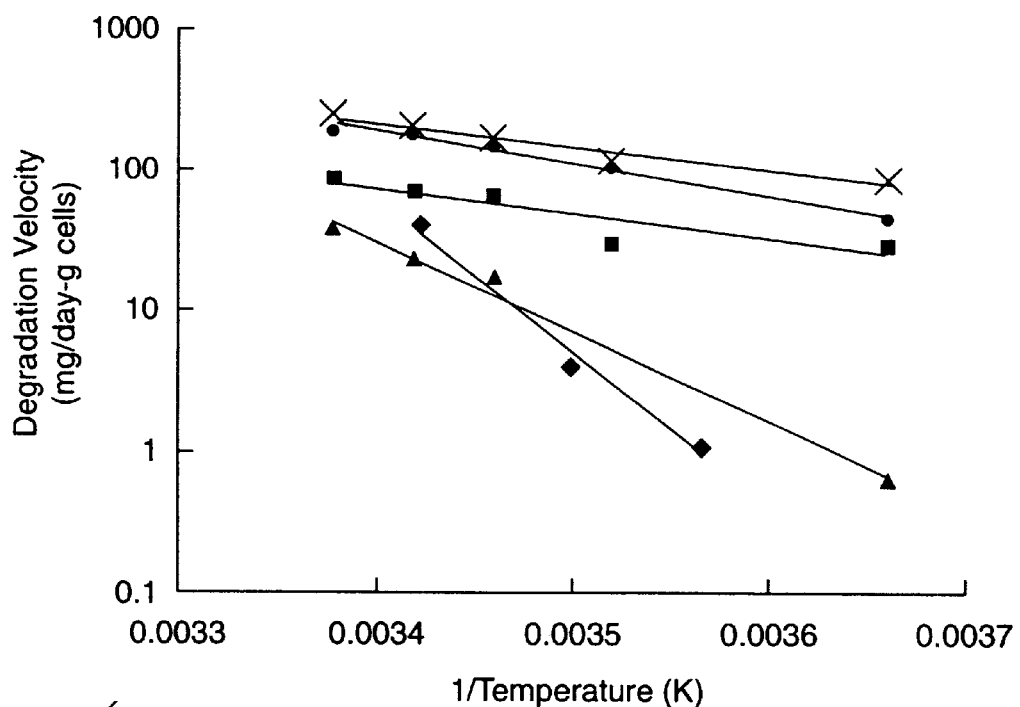
FIG. 7: Arrhenius plot of enzyme activity as a function of temperature. Enzyme was introduced in the form of killed, cross-linked, recombinant cells. Four of the data sets are laboratory data: the same cells used in the field study, stored for 7 months on the bench top as a moist cell pellet (■) or stored in neutralized cross-linking media (▲), and cells stored on the bench top for 8 months (●) or 9 months (X) in 30 mM phosphate buffer pH 7.2. The fifth data set is from the field remediation study (♦).

While the atrazine degrading ability of the recombinant organism is clearly temperature related, it is also related to other factors. To show this, enzyme activity as a function of temperature is presented as an Arrhenius plot in FIG. 7. In this form, the line slopes represent activation energy for the first order reaction. If this atrazine dechlorination reaction (catalyzed by whole stabilized cell suspension) was a simple first order reaction, the slopes of all the lines would be equal, but the slopes increase with increasing media complexity. Cells stored on the bench top in clear buffer retain the highest reaction activity. Reaction activity decreases when cells are stored in complex media, compared with that measured in the identical batch of cells stored as a moistened pellet. Finally, reaction activity decreases to a minimum for the cells mixed into soil at the field remediation site. This indicates that perhaps the drop in measurable activity may be due to chemical interactions occurring between the enzyme embedded in the cross-linked cells and other molecules present in the complex soil environment.

While it is true that the enzymatic activity of killed cells decreases in the more chemically complex soil environment, the present study has demonstrated that adding atrazine-degrading enzymes encapsulated in genetically engineered bacteria represents a viable option for treatment of accidental spills even under sub-optimal environmental conditions.

EXAMPLE 3

This example demonstrates the cross-linking of recombinant *E. coli* expressing a second hydrolytic enzyme, β-galactosidase, and the stability of the enzymatic activity of the cross-linked cells.

Materials and Methods

Growth and Cross-linking

The bacterial strain used was *Escherichia coli* DH5α (pUC119) (Viera, J. and J. Messing, *Gene,* 19, 259 (1982)). *E. coli* DH5α carries the lac deletion mutant lacZ(ΔM15), causing synthesis of a LacZ polypeptide missing amino acids 11–41. pUC119 encodes the amino terminal portion of the LacZ polypeptide, and when that amino terminal peptide is expressed, it complements the lacZ deletion mutation in *E. coli* DH5α to allow expression of active β-galactosidase.

*E. coli* DH5α (pUC119) was grown in 600 ml LB, 75 µg ampicillin per ml, in a 2 L flask with shaking overnight at 37° C. overnight to stationary phase. Cells were harvested by centrifugation, washed once, and resuspended in 50 mM sodium phosphate, pH 6.9, for native (non-cross-linked) cells, or in 50 mM $Na_2BO_4$—HCl, pH 9.0, 200 mM NaCl (borate buffer), for cross-linking. For cross-linking, cells at 4% wet weight/vol in borate buffer were mixed with an equal volume of 0.4% wt./vol glutaraldehyde in borate buffer, to give a final concentration of 2% cells and 0.2% glutaraldehyde, and stirred at 23° C. for 40 minutes. Then 1M Tris-HCl, pH 8.8, was added to a final concentration of 60 mM Tris, and the mixture was stirred for a further 40 minutes to react excess glutaraldehyde with Tris base. Cells were then harvested by centrifugation, washed, and resuspended in 50 mM sodium phosphate, pH 6.9.

Assays of β-galactosidase Activity

Native or cross-linked cell suspensions (8 µl, 20 µl, or 50 µl) at 4.3 mg wet wt. cells/ml, were added to 1 ml of 50 mM sodium phosphate, pH 6.9, 5 mM o-nitrophenol-β- galactoside, in a microcentrifuge tube, and incubated for 20 minutes at room temperature. The reaction was stopped by centrifuging out the cells. An 0.8 ml aliquot of the supernatant was withdrawn and mixed with 0.2 ml of 0.5 M $K_2CO_3$. The 450 nm absorbance was measured to determine the concentration of o-nitrophenol, using $\epsilon_{450}=2.91$ mM$^{-1}$.

Results

The measured β-galactosidase activities of the native and cross-linked cells initially, and after storage for 16 hours in phosphate buffer at room temperature or at 37° C. are reported in Table 11.

TABLE 11

β-Galactosidase Activity (μmoles/min/mg cells).

|  | Native Cells | 0.2% Glutaraldehyde Cross-Linked Cells |
|---|---|---|
| Initial | 13.0 | 54.4 |
| 23° C. Overnight | 14.7 | 68.7 |
| 37° C. Overnight | 25.1 | 30 |

The cross-linked cells actually had a higher measured enzyme activity than the native cells. This is probably because the optimal pH for β-galactosidase is acidic, and the assays were done in pH 6.9, whereas the cytoplasmic pH in intact cells is above 8. Cross-linking permeabilizes the cell membrane, so that the enzyme experiences the buffer pH of 6.9. In native cells, in contrast, the enzyme would be operating in the cytoplasmic pH of approximately 8, which is suboptimal for this enzyme. That would also be a possible explanation why in native cells the measured enzyme activity level increased after storage overnight at 37° C.: the cell membrane may have been partially permeabilized by that treatment. In any case, cross-linking caused little if any loss of enzyme activity, since the cross-linked cells had approximately four times the measured enzyme activity of the native cells.

The cross-linked cells retained more than 50% of their initial enzyme activity after storage at 37° C. overnight, showing that the enzyme activity is rather stable after cross-linking.

These data show that hydrolytic enzymes in general retain high levels of enzyme activity after cross-linking of microbial cells, and that the enzyme activity of hydrolytic enzymes in general in cross-linked cells is stable.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE LISTING FREE TEXT

SEQ ID NOs:1–2 oligonucleotide primer

What is claimed is:

1. A method for remediating a compound in a sample, the method comprising:

providing killed cross-linked microbes comprising an exogenous polynucleotide comprising a coding region encoding a hydrolase that degrades an s-triazine, wherein the microbes retain at least about 30% hydrolase enzymatic activity compared to the hydrolase enzymatic activity of the microbes that are not killed; and contacting a sample comprising the s-triazine with the microbes under conditions effective to decrease the concentration of the s-triazine in the sample relative to the concentration of the s-triazine in a sample not contacted with the microbes.

2. The method of claim 1 wherein the microbes are cross-linked with a cross-linking agent selected from the group consisting of glutaraldehyde, formalin, and iodine.

3. The method of claim 1 wherein the sample is selected from the group consisting of soil, water, and a combination thereof.

4. The method of claim 1 wherein the microbes are selected from the group consisting of $E.$ $coil$ and $P.$ $aeruginosa$.

5. The method of claim 1 further comprising measuring the concentration of the compound in the sample after contacting the sample with the microbes.

6. The method of claim 1 wherein the cross-linked microbes are attached to a support.

7. A method for remediating a compound in a sample, the method comprising:

providing killed cross-linked microbes comprising an exogenous polynucleotide comprising a coding region encoding a hydrolase that degrades an s-triazine, wherein the complement of the nucleotide sequence of the coding region hybridizes to the nucleotide sequence set forth at nucleotides 236 to 1660 of SEQ ID NO:3 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS, and wherein the microbes retain at least about 30% hydrolase enzymatic activity compared to the hydrolase enzymatic activity of the microbes that are not killed; and contacting a sample comprising the s-triazine with the microbes under conditions effective to decrease the concentration of the s-triazine in the sample relative to the concentration of the s-triazine in a sample not contacted with the microbes.

8. The method of claim 7 wherein the s-triazine is selected from the group of atrazine, desethylatrazine, deisopropylatrazine, desethylhydroxyatrazine, desisopropylhydroxyatrazine, desethyldesisopropylatrazine, simazine, terbuthylazine, melamine, ammelide, ammeline, prometryn, ametryn, propazine, cyanuric acid, terbutryn, cyanazine, propazine, simatone, and cyromazine.

9. A method for remediating a compound in a sample, the method comprising;

providing killed cross-linked microbes comprising an exogenous polynucleotide comprising a coding region encoding a hydrolase that degrades atrazine, wherein the complement of the nucleotide sequence of the coding region hybridizes to the nucleotide sequence set forth at nucleotides 236 to 1660 of SEQ ID NO:3 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS, and wherein the microbes retain at least about 30% hydrolase enzymatic activity compared to the hydrolase enzymatic activity of the microbes that are not killed; and contacting a sample comprising the atrazine with the microbes under conditions effective to decrease the concentration of the atrazine in the sample relative to the concentration of the atrazine in a sample not contacted with the microbes.

10. A method for remediating a compound in a sample, the method comprising:

providing killed cross-linked microbes comprising an exogenous polynucleotide comprising a coding region encoding a hydrolase that degrades atrazine, wherein the nucleotide sequence of the coding region comprises nucleotides 236 to 1660 of SEQ ID NO:3, and wherein the microbes retain at least about 30% hydrolase enzymatic activity compared to the hydrolase enzymatic activity of the microbes that are not killed; and contacting a sample comprising the atrazine with the microbes under conditions effective to decrease the concentration of the atrazine in the sample relative to the concentration of the atrazine in a sample not contacted with the microbes.

11. Killed cross-linked microbes comprising a polynucleotide comprising a coding region encoding a hydrolase that degrades an s-triazine, wherein the cross-linked microbes retain at least about 30% hydrolase enzymatic activity compared to the hydrolase enzymatic activity of the microbes that are not killed.

12. Killed cross-linked microbes comprising a polynucleotide comprising a coding region encoding a hydrolase that degrades an s-triazine, wherein the complement of the nucleotide sequence of the coding region hybridizes to the nucleotide sequence set forth at nucleotides 236 to 1660 of SEQ ID NO:3 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS, and wherein the microbes retain at least about 30% hydrolase enzymatic activity compared to the hydrolase enzymatic activity of the microbes that are not killed.

13. Killed cross-linked microbes comprising a polynucleotide comprising a coding region encoding a hydrolase that degrades atrazine, wherein the complement of the nucleotide sequence of the coding region hybridizes to the nucleotide sequence set forth at nucleotides 236 to 1660 of SEQ ID NO:3 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS, and wherein the microbes retain at least about 30% hydrolase enzymatic activity compared to the hydrolase enzymatic activity of the microbes that are not killed.

14. Killed cross-linked microbes comprising a polynucleotide comprising a coding region encoding a hydrolase that degrades atrazine, wherein the nucleotide sequence of the coding region comprises nucleotides 236 to 1660 of SEQ ID NO:3, and wherein the microbes retain at least about 30% hydrolase enzymatic activity compared to the hydrolase enzymatic activity of the microbes that are not killed.

\* \* \* \* \*

UNITED STATES PATENT AND TRADEMARK OFFICE
CERTIFICATE OF CORRECTION

PATENT NO.   : 6,673,582 B2
DATED        : January 6, 2004
INVENTOR(S)  : McTavish, Hugh It is certified that error appears in the above-identified patent and that said Letters Patent is hereby corrected as shown below:

<u>Column 14,</u>
Line 17, delete "GenBank accession numberr U55933" and insert -- SEQ ID NO:3 --

Signed and Sealed this

Eighth Day of June, 2004

JON W. DUDAS
*Acting Director of the United States Patent and Trademark Office*